(12) United States Patent
Xiang et al.

(10) Patent No.: US 7,276,902 B1
(45) Date of Patent: Oct. 2, 2007

(54) DETECTION WITH EVANESCENT WAVE PROBE

(75) Inventors: Xiao-Dong Xiang, Danville, CA (US); Haitao Yang, San Jose, CA (US); Gang Wang, San Jose, CA (US)

(73) Assignee: Intematix Corporation, Fremont, CA (US)

( * ) Notice: Subject to any disclaimer, the term of this patent is extended or adjusted under 35 U.S.C. 154(b) by 0 days.

(21) Appl. No.: 11/542,891

(22) Filed: Oct. 3, 2006

Related U.S. Application Data

(60) Division of application No. 10/833,186, filed on Apr. 28, 2004, now Pat. No. 7,148,683, which is a continuation-in-part of application No. 10/759,745, filed on Jan. 16, 2004, now Pat. No. 6,946,835, which is a division of application No. 10/071,563, filed on Feb. 9, 2002, now Pat. No. 6,693,426.

(60) Provisional application No. 60/546,056, filed on Feb. 18, 2004, provisional application No. 60/465,736, filed on Apr. 28, 2003, provisional application No. 60/344,427, filed on Oct. 25, 2001.

(51) Int. Cl.
*G01V 3/00* (2006.01)

(52) U.S. Cl. ...................... 324/300; 324/304

(58) Field of Classification Search ........ 324/300–322; 600/410–445
See application file for complete search history.

(56) References Cited

U.S. PATENT DOCUMENTS

| | | | |
|---|---|---|---|
| 5,821,410 A | 10/1998 | Xiang et al. | |
| 5,936,237 A | 8/1999 | van der Weide | |
| 6,097,188 A | 8/2000 | Sweedler et al. | |
| 6,173,604 B1 | 1/2001 | Xiang et al. | |
| 6,182,499 B1 | 2/2001 | McFarland et al. | |
| 6,311,086 B1 | 10/2001 | Ardenkjaer-Larsen et al. | |
| 6,346,290 B1 | 2/2002 | Schultz et al. | |
| 6,401,519 B1 | 6/2002 | McFarland et al. | |
| 6,410,331 B1 | 6/2002 | Schultz et al. | |
| 6,420,179 B1 | 7/2002 | Schultz et al. | |
| 6,463,186 B1 | 10/2002 | Li | |
| 6,472,869 B1 | 10/2002 | Upschulte et al. | |
| 6,532,806 B1 | 3/2003 | Xiang et al. | |
| 6,538,454 B1 | 3/2003 | Frenkel et al. | |
| 6,597,185 B1 | 7/2003 | Talanov et al. | |
| 6,614,227 B2 | 9/2003 | Ookubo | |
| 6,641,940 B1 | 11/2003 | Li et al. | |
| 6,649,413 B1 | 11/2003 | Schultz et al. | |
| 6,680,617 B2 | 1/2004 | Moreland et al. | |
| 6,686,205 B1 | 2/2004 | Schultz et al. | |

(Continued)

OTHER PUBLICATIONS

Lacey et al., "High Resolution NMR Spectroscopy of Sample Volumes from 1 NL to 10 μL," *Chemical Reviews*, Feb. 24, 1999, pp. A-T.

(Continued)

*Primary Examiner*—Brij B. Shrivastav
(74) *Attorney, Agent, or Firm*—Buchanan Ingersoll & Rooney LLP

(57) ABSTRACT

Methods and systems for spatially resolved spin resonance detection in a sample of material are disclosed. Also disclosed are methods and systems for spatially resolved impedance measurements in a sample of material. The disclosed methods and samples can be used in screening of plurality of biological, chemical and material samples.

9 Claims, 18 Drawing Sheets

U.S. PATENT DOCUMENTS

| | | | |
|---|---|---|---|
| 6,693,426 | B1 | 2/2004 | Xiang et al. |
| 6,794,052 | B2 | 9/2004 | Schultz et al. |
| 6,822,454 | B2 | 11/2004 | Peck et al. |
| 6,825,645 | B2 | 11/2004 | Kelly et al. |
| 6,864,201 | B2 | 3/2005 | Schultz et al. |
| 6,924,150 | B1 | 8/2005 | Xiang et al. |
| 6,946,835 | B1 | 9/2005 | Xiang et al. |
| 6,957,565 | B2 | 10/2005 | Matsiev et al. |
| 7,034,091 | B2 | 4/2006 | Schultz et al. |
| 7,073,370 | B2 | 7/2006 | Matsiev et al. |
| 7,148,683 | B2 * | 12/2006 | Xiang et al. ............... 324/300 |
| 2001/0055669 | A1 | 12/2001 | Schultz et al. |
| 2002/0175693 | A1 | 11/2002 | Starr et al. |
| 2002/0197645 | A1 | 12/2002 | Martin |
| 2003/0162179 | A1 | 8/2003 | Polyrailo et al. |
| 2004/0014077 | A1 | 1/2004 | Schultz et al. |

OTHER PUBLICATIONS

Soohoo, "A Microwave Magnetic Microscope," *Journal of Applied Physics*, Suppl. to vol. 33, No. 3, Mar. 1962, pp. 1276-1277.

Binnig et al., "Atomic Force Microscope," *Phys. Rev. Lett.*, 56(9), Mar. 3, 1986, pp. 930-933.

Glover et al., "Limits to magnetic Resonance Microscopy," *Rep. Prog. Phys.* 65 (2002), pp. 1489-1511.

Sarid et al., "Improved Atomic Force Microscope Using a Laser Diode Interferometer," *Rev. Sci. Instrum.* 63(8), Aug. 1992, pp. 3905-3908.

Zhong et al., "Fractured Polymer/Silica Fiber Surface Studied by Tapping Mode Atomic Force Microscopy," *Surface Science Letters*, 290 (1993), pp. L688-L692.

Takata, "Whole Electronic Cantilever Control for Atomic Force Microscopy," *Rev. Sci. Instrum.* 64(9), Sep. 1993, pp. 2598-2600.

Van Der Werf, et al., "Compact Stand-Alone Atomic Force Microscope," *Rev. Sci. Instrum.* 64(10), Oct. 1993, pp. 2892-2897.

Grober et al., "Design and Implementation of a Low Temperature Near-Field Scanning Optical Microscope," *Rev. Sci. Instrum.* 65(3), Mar. 1994, pp. 626-631.

Leong et al., "Shear Force Microscopy With Capacitance Detection for Near-Field Scanning Optical Microscopy," *Appl. Phys. Lett.* 66(11), Mar. 13, 1995, pp. 1432-1434.

Karrai et al., "Piezoelectric Tip-Sample Distance Control for Near Field Optical Microscopes," *Appl. Phys. Lett.* 66(14), Apr. 3, 1994, pp. 1842-1844.

Tarrach et al., "Design and Construction of a Versatile Scanning Near-Field Optical Microscope for Fluoresence Imaging of Single Molecules," *Rev. Sci. Instrum.* 66(6), Jun. 1995, pp. 3569-3575.

Brunner et al., "Distance Control in Near-Field Optical Cicroscopy With Piezoelectrical Shear Force Detection Suitable for Imaging in Liquids," *Rev. Sci. Instrum.*, 68(4), Apr. 1997, pp. 1769-1772.

Gao et al., "Quantative Microwave Near-Field Microscopy of Dielectric Properties," Rev. Sci. Instrum., 69(11), Nov. 1998, pp. 3846-3851.

Cho et al., "Scanning Nonlinear Dielctric Microscopy With Contact Sensing Mechanism for Observation on Nanometer Sized Ferorelectric Domains," *Jpn. J. Appl. Phys.*, vol. 38 (1999), pp. 5689-5694.

Giessibl, "Atomic Resolution of Si(111)-(7x7) by Noncontact Atomic Force Miscroscopy With a Force Sensor Based on a Quartz Tuning Fork," *Appl. Phys. Lett.* 76(11), Mar. 13, 2000, pp. 1470-1472.

Orai et al., "High-Sensitivity Noncontact Atomic Force Miscroscope/Scanning Tunneling (nc AFM/STM) operating at subangstrom Oscillation Amplitudes for Atomic Resolution Imaging and Force Spectroscopy," Rev Sci. Instum., 74(8), Aug. 2003, pp. 3656-3663.

Hauser et al., "Magnetoresistors," *Magnet Sensors and Magnetometers*, Chapter 4, Ed. Pavel Ripka, Artech House, 2001, pp. 129-171.

Popvic et al., "Hall Effect Magnetic Sensors," *Magnet Sensors and Magnetometers*, Chapter 5, Ed. Pavel Ripka, Artech House, 2001, pp. 173-242.

Witte et al., "X-Band Elektronenspinresonanz mit Blochscher Messanordnung," Appl. Phys., vol. 2, No. 2, Aug. 1973, pp. 63-70 9English Abstract included).

Wallace et al., "Microstrip Resonators for Electron-Spin Resonance," *Rev. Sci. Instrum.*, vol. 62, No. 7, Jul. 1991, pp. 1754-1766.

Furusawa, et al., "Distribution of Nitrogen and Nickel in a Synthetic Diamond Crystal Observed With Scanning ESR Imaging," *J. Phys. Soc. Jpn.*, vol. 59, No. 7, Jul. 1990, pp. 2340-2343.

Brossel et al., "Gréation Optique D'Une Inégalité de Population Entre Les Sous-Niveaux Zeeman de L'état Fondamental des Atomes," *J. Phys. Radium*, vol. 13, No. 12, Dec. 1952, pp. 668-669.

Kastler et al., "Quelques Suggestions Concernmant la Production Optique et al. Detection Optique D'Une Inegalite de Population des Niveaux de Quantification Spatiale des Atomes Application a L'Experience de Stern et Gerlach et a la Resonance Magnetique," *J. Phys. Radium*, vol. 11, No. 6, Jun. 1950, pp. 255-265.

Rafferty, "High-Field NMR of Adsorbed Xenon Polarized by Laser Pumping," *Phys. Rev. Lett.*, vol. 66, No. 5, Feb. 4, 1991, pp. 584-587.

Kohler et al., "Single Molecule Electron Paramagnetic Resonance Spectroscopy: Hyperfine Splitting Owing to a Single Nucleus," *Science*, vol. 268, Jun. 9, 1995, pp. 1457-1460.

Wrachtrup et al., "Optical Detection of Magnetic Resonance in a Single Molecule," *Nature*, vol. 363, No. 6426, May 20, 1993, pp. 244-245.

* cited by examiner

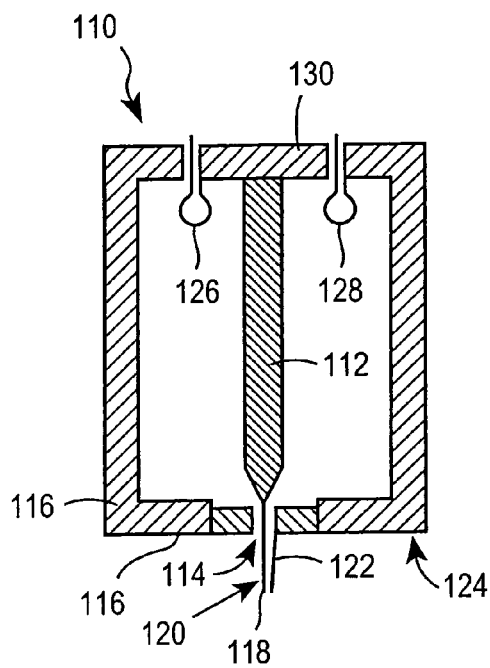
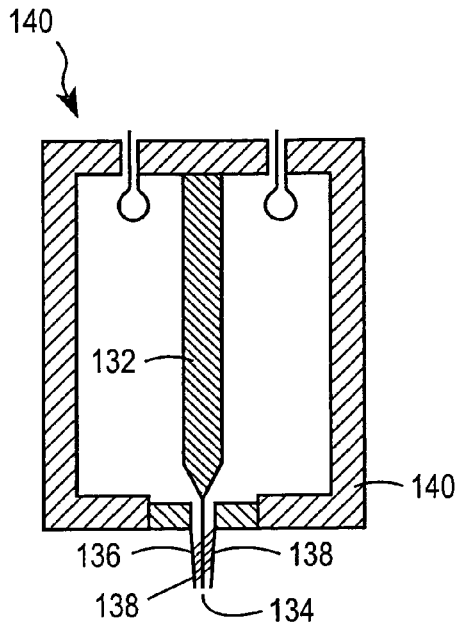
FIG. 11      FIG. 12
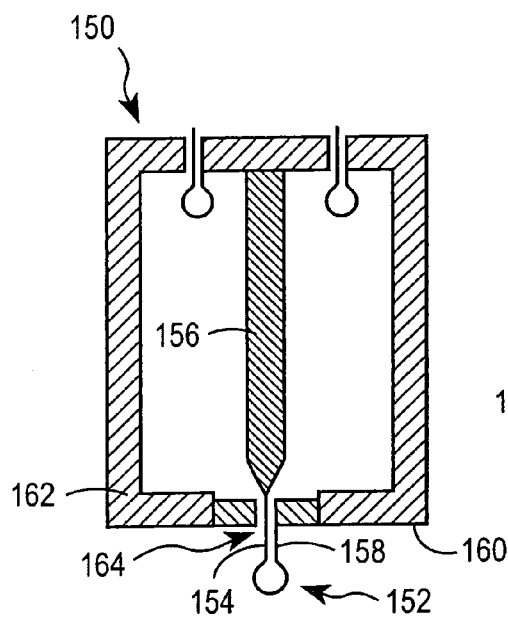
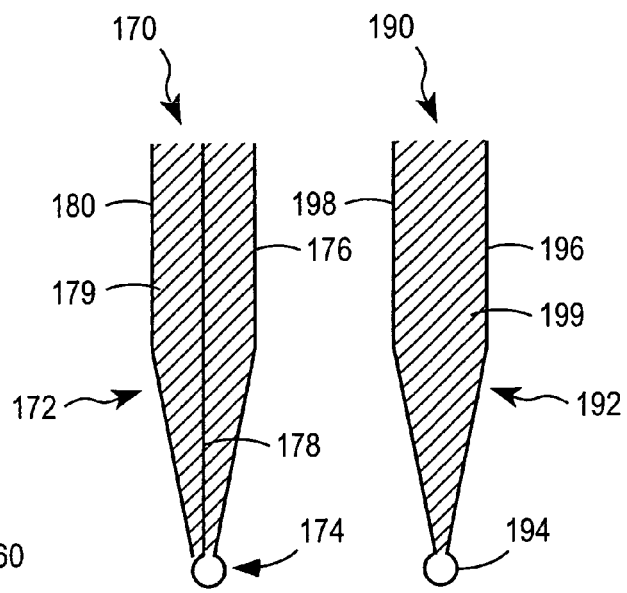
FIG. 13      FIG. 14A   FIG. 14B

DETECTION WITH EVANESCENT WAVE PROBE

CROSS REFERENCE TO RELATED APPLICATIONS

This application is a divisional of U.S. patent application Ser. No. 10/833,186, filed Apr. 28, 2004 now U.S. Pat. No. 7,148,683, which is a continuation-in-part of U.S. patent application Ser. No. 10/759,745, filed on Jan. 16, 2004 now U.S. Pat. No. 6,946,835, which is a divisional of Ser. No. 10/071,563 now U.S. Pat. No. 6,693,426, filed on Feb. 9, 2002, which claims the benefit of U.S. Provisional Patent Application No. 60/344,427, filed on Oct. 25, 2001. This application also claims the benefit of U.S. Provisional Patent Application No. 60/465,736, filed on Apr. 28, 2003, and claims the benefit of U.S. Provisional Application No. 60/546,056, entitled "Integration of AFM/STM into Evanescent Microwave Probe" filed on Feb. 18, 2004. The entire content of each of these applications is herein incorporated by reference.

FIELD

This disclosure relates to the fields of high-resolution and high-sensitivity spin resonance detection (e.g., electron spin resonance (ESR), ferromagnetic resonance (FMR), and nuclear spin resonance (NMR)), impedance detection and/or scanning probe microscopy (SPM). More specifically, this disclosure relates to apparatuses and methods incorporating one or more of spin resonance detection, impedance detection and/or atomic force microscopy and evanescent wave probes.

BACKGROUND

In the discussion of the state of the art that follows, reference is made to certain structures and/or methods. However, the following references should not be construed as an admission that these structures and/or methods constitute prior art. Applicants expressly reserve the right to demonstrate that such structures and/or methods do not qualify as prior art against the present invention.

For many applications in materials and bioscience research, spatially resolved spin resonance detection with high sensitivity is desired. Conventional spin resonance detection experiments are usually performed by placing a sample in a microwave cavity or a pair of RF coils situated in a strong DC or substantially static magnetic field that is perpendicular to the microwave or RF magnetic field. High power microwave or RF radiation excites the coherent spin precession. Precessing spin-induced induction and absorption signals are picked up by a cavity or a coil and detected by a diode mixer. Although the intrinsic sensitivity is limited by cavity Johnson noise, which is near single-spin detection, this level of detection has never been possible practically. Primary limitations in a conventional experiment are large background noise from high power excitation signal generated by high-power klystron source (need to excite spin in bulk samples) and diode detector noise since a low noise amplifier cannot be employed before a diode detector without being saturated by high level excitation signal pick up at a detection port.

Detailed nano-scale, molecular-level knowledge of the relationships between structure, dynamics, and function of biological macromolecules is a prerequisite for and an integral part of the ability to proceed toward the understanding of the basic principles underlying the regulation of living cells. One major research interest in the biomedical community is how the structure and internal dynamics of proteins lead to biological function. Despite enormous progress in the past decades, there are still major unresolved questions regarding molecular events associated with protein folding. To identify the underlying biochemical processes, magnetic resonance technology has been regarded as an effective probe to determine the structure of proteins. Similar relationships and interests occur in chemistry and materials science.

Spectroscopy and imaging technologies based on magnetic resonance, e.g., electron magnetic resonance (ESR) and nuclear magnetic resonance (NMR), have in the past contributed to fundamental characterization of molecular structure as well as medical diagnosis. Dramatic advances in proteomics and biomedical science have raised challenging demands for nano-scale spatially resolved magnetic resonance spectroscopy and imaging technology with increased sensitivity.

Conventional NMR techniques can determine molecular structure of a large ensemble of homogenous molecules through precise measurement of a chemical shift of nuclear spin resonance in a uniform magnetic field. Non-uniformity of the magnetic field tends to smear out the small chemical shift and reduce, if not eliminate, the effectiveness of a NMR instrument in structure determination. In this situation, NMR machines only have the capability of structural determination for a large volume of homogenous specimen and do not have any spatial resolution.

In contrast, MRI techniques have the capability of imaging with certain spatial resolution (usually in mm range). This capability is realized through a high magnetic field gradient generated in the specimen and the spatial resolution is proportional to the degree of the gradient. The presence of a field gradient smears out chemical shifts and different resonance peaks become one broad peak. Consequently, conventional MRI imaging technique lacks the capability of spectroscopy and structural determination. In the meantime, chemical shifts in nuclear spin resonance also limit the spatial resolution of MRI (10 ppm of typical chemical shift determines that the MRI spatial resolution to be mm).

SUMMARY

Exemplary systems, apparatus and methods provide evanescent microwave or RF wave excitation and detection of spin resonance and, in the case of time-continuous spin resonance detection, optional cancellation of excitation signal at the detection port, and in the case of time-resolved spin resonance detection, optional relaxation and/or resonant frequency detection.

Therefore, spatially resolved (with spatial resolution better than the wavelength of the excitation signal) spin resonance detection with high sensitivity limited by the low noise amplifier or Johnson noise of the resonator can be realized.

In one exemplary embodiment, an evanescent microwave orthogonal resonator probe is designed to achieve high spatial resolution and high sensitivity spin resonance detection. The probe design uses a bimodal transmission-type (or waveguide/cavity type) resonator with input and output coupled to orthogonal modes. The purpose of the design is to isolate excitation and detection modes and dramatically reduce background signal. This will allow low noise amplification to be implemented to achieve Johnson noise limited sensitivity without amplifier saturation. Only a very small spin resonance induced signal power is coupled to the probe output and amplified. Spin resonance signal is proportional to excitation RF or microwave field intensity $(H_{rf})^2$ below saturation threshold. In conventional spin resonance studies, very high power (klystron source) is required to reach the saturation level. In this design, only very small microwave power is needed to excite small volume of sample near the tip (or aperture) with very high field intensity. This will dramatically reduce the background noise of microwave source because a low noise level generator can be used. Because both excitation and pickup volume are small, other extrinsic noises will also be dramatically reduced. A typical klystron source has FM noise around −30 dB while a high quality microwave synthesizer proposed to implement in this project has FM noise around −110 dB.

In another exemplary embodiment, internal or external cancellation schemes are used to cancel the large excitation signal that would otherwise be detected at the detection port. In an external cancellation scheme, two substantially identical transmission line resonators (or cavity/waveguide resonators) with the same resonant frequency and insertion loss are used. One of the resonators has an evanescent wave probe to interact with sample (excite and detect spin resonance). The evanescent probe may be (1) a metal tip connected to the center conductor of a transmission type resonator, (2) a metal loop connected between the center conductor and ground shielding; or (3) an aperture on the shielding wall of a cavity or waveguide resonator. The other resonator serves as a reference or "dummy" resonator. The outputs of the two resonators are received by a power combiner with a 180° phase-shift for one of the input signals, thereby forming a difference of the output signals. This signal combiner cancels the large background (excitation) signal, and a low noise amplifier can be employed to increase the sensitivity. As the evanescent probe excites the spin resonance, the probe-sample interaction breaks the symmetry and precise cancellation, and the resulting small changes represent the spin resonance signal to be detected.

In the case of an optional internal cancellation scheme, the pick up coupling will be positioned at the node of the mode of either a transmission type or cavity type resonator, equipped with evanescent probe as described above. As the evanescent probe excites the spin resonance, the induced magnetization will change the node position in the resonator. As a consequence, the pick up coupling will detect the small signal due to this spin resonance induced effect without coupling to the large excitation background signal. Low noise amplifier can then boost the signal to achieve high sensitivity in both cases.

In each of these situations, in order to further increase the sample volume sensitivity, (e.g., increase the spin states population difference, especially for NMR at room temperature), optical pumping is preferably used. An integrated optical path is designed to apply optical pumping.

In a further embodiment, an optical pumping and detection scheme is employed, using an evanescent electromagnetic wave excitation. The integrated evanescent microwave probe optical microscope system (EMP-OM) can provide microwave induced optical detection for optically pumped spin resonance detection. Spatial resolution in both operating modes is achieved by an evanescent microwave (or radio wave) probe, which only excites and picks up spin resonance induced microwave (or RF) induction and absorption signals in a very small sample volume (as small as $nm^3$) proportional to the cube of probe radius.

Additional exemplary systems, apparatus and methods provide evanescent microwave or RF wave excitation and detection of spin resonance in combination with impedance and/or scanning probe microscopy (SPM), e.g., atomic force microscopy (AFM), scanning tunneling microscopy (STM), scanning near-field optical microscopy (SNOM) and magnetic force microscopy (MFM), to measure properties and structures and to provide simultaneously high spatial resolution, high contrast topography and high sensitivity spin magnetic resonance spectroscopy.

One exemplary embodiment of a system for making spatially resolved spin-resonance spectroscopic measurements in a material sample comprises a first magnetic field source, the first magnetic field source generating a first magnetic field in a sample region, wherein the first magnetic field has a field component along a first direction at a first location in the sample region, a second magnetic field source, the second magnetic field source generating a second magnetic field in the sample region, the second magnetic field having a field component along a second direction in the sample region, the second direction being substantially perpendicular to the first direction, wherein the first and second magnetic fields interact with at least one spin of at least one atomic constituent of a sample at the first location to produce a spin resonance of the at least one spin, and an evanescent wave probe located adjacent to the first location, the evanescent wave probe sensing the spin resonance of the at least one spin and generating a spin resonance signal, wherein the spin resonance is nuclear magnetic resonance.

An exemplary method for spatially resolved spin resonance spectroscopy in a material sample comprises exciting a sample with a first magnetic field, the first magnetic field having a field component along a first direction at a first location on the sample, applying a second magnetic field to the sample, the second magnetic field having a field component along a second direction, the second direction being substantially perpendicular to the first direction, wherein the first magnetic field and the second magnetic field interact with at least one spin for at least one atomic constituent at the first location to produce a spin resonance, and sensing the spin resonance of the at least one spin using an evanescent wave probe located adjacent to the first location, wherein the spin resonance is nuclear magnetic resonance.

Another exemplary embodiment of an apparatus for making spatially resolved spin-resonance spectroscopic measurements in a material sample comprises a first magnetic field source, the first magnetic field source generating a first magnetic field in a sample region, wherein the first magnetic field has a field component along a first direction at a first location in the sample region, a second magnetic field source, the second magnetic field source generating a second magnetic field in the sample region, the second magnetic field having a field component along a second direction in the sample region, the second direction being substantially perpendicular to the first direction, wherein the first and second magnetic fields interact with at least one spin of at least one atomic constituent of a sample at the first location to produce a spin resonance of the at least one spin, and an evanescent wave probe located adjacent to the first location, the evanescent wave probe sensing the spin resonance of the at least one spin and generating a spin resonance signal, wherein the spin resonance is selected from a group consisting of electron spin resonance and ferromagnetic resonance, wherein sensing the spin resonance includes making a time-resolved measurement of at least one property of the spin resonance.

Another exemplary method for spatially resolved spin resonance spectroscopy in a material sample comprises exciting a sample with a first magnetic field, the first magnetic field having a field component along a first direction at a first location on the sample, applying a second magnetic field to the sample, the second magnetic field having a field component along a second direction, the second direction being substantially perpendicular to the first direction, wherein the first magnetic field and the second magnetic field interact with at least one spin for at least one atomic constituent at the first location to produce a spin resonance, and sensing the spin resonance of the at least one spin using an evanescent wave probe located adjacent to the first location, wherein the spin resonance is selected from a group consisting of electron spin resonance and ferromagnetic resonance, wherein sensing the spin resonance includes making a time-resolved measurement of at least one property of the spin resonance.

A further exemplary embodiment of an apparatus for spatially resolved impedance in a material sample comprises an evanescent wave probe positionable adjacent to a sample location, the evanescent wave probe configured to emit an evanescent wave including at least one of a time varying amplitude and a time varying phase, a detection circuit, the detection circuit detecting a time-resolved change in a resonance frequency of the evanescent wave probe and of a change in a quality factor of the evanescent wave probe, and a processing system, the processing system processing the change in the resonance frequency and the change in a quality factor to produce an impedance measurement.

A further exemplary method of measuring a spatially resolved impedance in a material sample comprises moving a tip of an evanescent wave probe toward a surface of a sample to place the surface of the sample within a sensing distance, generating an evanescent wave with the evanescent wave probe, the evanescent wave including at least one of a time varying amplitude and a time varying phase, making a time resolved measurement of a change in a resonant frequency of the evanescent wave probe and of a change in a quality factor of the evanescent wave probe, and determining an impedance of the sample based on the change in the resonant frequency and based on the change in the quality factor.

Another exemplary embodiment of a system for making spatially resolved spin-resonance spectroscopic measurements in a material sample comprises a first magnetic field source, the first magnetic field source generating a first magnetic field in a sample region, wherein the first magnetic field has a field component along a first direction at a first location in the sample region, a second magnetic field source, the second magnetic field source generating a second magnetic field in the sample region, the second magnetic field having a field component along a second direction in the sample region, the second direction being substantially perpendicular to the first direction, wherein the first and second magnetic fields interact with at least one spin of at least one atomic constituent of a sample at the first location to produce a spin resonance of the at least one spin, and an magnetic sensor located adjacent to the first location, the magnetic sensor sensing the spin resonance of the at least one spin and generating a spin resonance signal, wherein the magnetic sensor is sized to sense a sample volume of micron$^3$ or less and the spin resonance is nuclear magnetic resonance.

An additional exemplary method for spatially resolved spin resonance spectroscopy in a material sample comprises exciting a sample with a first magnetic field, the first magnetic field having a field component along a first direction at a first location on the sample, applying a second magnetic field to the sample, the second magnetic field having a field component along a second direction, the second direction being substantially perpendicular to the first direction, wherein the first magnetic field and the second magnetic field interact with at least one spin for at least one atomic constituent at the first location to produce a spin resonance, and sensing the spin resonance of the at least one spin using magnetic sensor located adjacent to the first location, wherein the magnetic sensor is sized to sense a sample volume of a micron$^3$ or less and the spin resonance is nuclear magnetic resonance.

An exemplary method of screening a plurality of biological, chemical or material samples comprises making a plurality of spin-resonance spectroscopic measurements corresponding to the plurality of samples according to any one of exemplary methods disclosed herein and selecting at least one of the plurality of samples based on the plurality of spin-resonance spectroscopic measurements.

A further exemplary method of screening a plurality of biological, chemical or material samples comprises making a plurality of spatially resolved impedance measurements corresponding to the plurality of samples according to any one of exemplary methods disclosed herein and selecting at least one of the plurality of samples based on the plurality of spatially resolved impedance measurements.

An "evanescent microwave probe" as referred to herein is defined as a probe that emits substantially an evanescent wave (non-propagating wave). An evanescent wave as referred to herein is an electromagnetic wave with an imaginary component in its wave vector. The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide.

BRIEF DESCRIPTION OF THE DRAWING

The objects and advantages of the invention will become apparent from the following detailed description of preferred embodiments thereof in connection with the accompanying drawings in which like numerals designate like elements and in which:

FIGS. 11 to 13 illustrate various exemplary embodiments of an evanescent wave probe.

FIGS. 14A and 14B illustrate two exemplary embodiments of a transmission line type evanescent wave probe.

DETAILED DESCRIPTION

Figure 1:
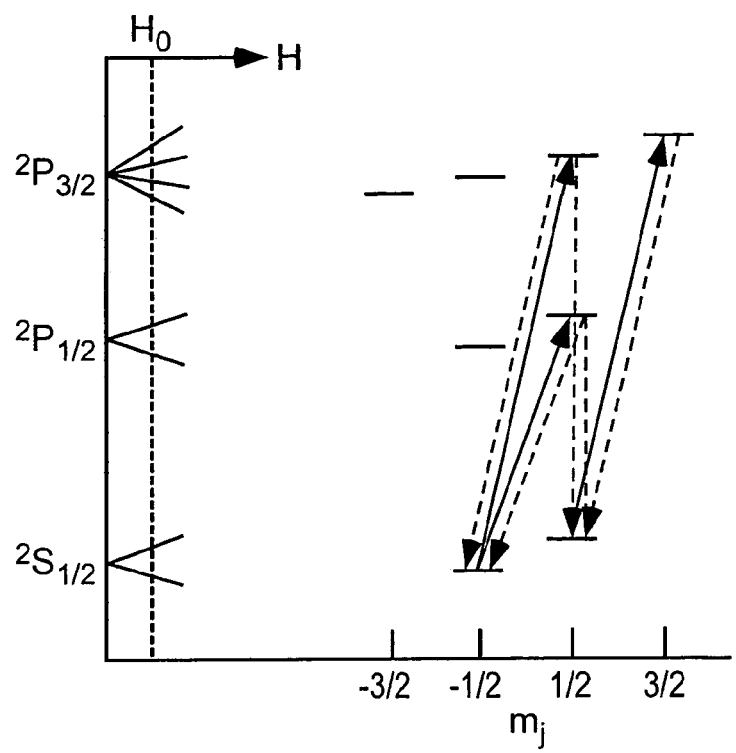
FIG. 1 graphically illustrates fine structure of the resonance radiation states for a typical alkali metal.

One way to improve detection sensitivity in conventional NMR is to employ a resonator with degenerate orthogonal modes. In this case, input and output channels are coupled to these orthogonal modes respectively. Ideally, the pick up coupling only picks up a signal due to spin resonance induced effects from the sample, not from the large excitation signal. Ideally, because the power fed from input channel is not coupled to the output channel, one gets a near zero-power background. The low noise amplifier can therefore be employed without being saturated. When the magnetic resonance is excited, the resonance destroys the symmetry of those orthogonal modes and couples small power to the mode that is coupled with the output channel. This small power due to the symmetry breaking is the signal power that is desired to be detected.

Witte et al. reported a design of an X-band induction spectrometer with a bimodal cavity with 110 dB isolation between transmitter and receiver [A. Witte, G. Laukien and P. Dullenkopf, Appl. Phys. 2, 63-70 (1973)]. Wallace and Silsbee have also demonstrated a microstrip resonator for thin film measurement [W. J. Wallace and R. H. Silsbee, RSI 62 (7), 1754 (1991)]. However, in these studies only bulk samples or large area thin film samples are involved.

In a different direction, spatially resolved spin resonance detection has been attempted by employing evanescent electromagnetic wave detector [R. F. Soohoo, J. of Applied Physics, Vol. 33, 1276 (1962) and Masahiro Fursawa and Motoji Ikeya, J. of the Physical Society of Japan, Vol. 59, 2340 (1990)]. The basic approach in these studies is to radiate the sample local area with evanescent electromagnetic wave from an aperture on the wall of microwave resonator in applied DC magnetic field. The resolution achieved is around mm range and the sensitivity is relatively low.

In another different direction, optical spin resonance pumping and detection has been developed. One of the major problems for spin resonance detection is the small population difference that exists between two adjacent Zeeman levels governed by Boltzmann statistics:

$$\Delta n = 1 - \exp\left(\frac{g\mu B}{kT}\right) \qquad (1)$$

where g is gyromagnetic ratio, $\mu$ is the nuclear magneton $\mu_N$ for NMR, or Bohr magneton $\mu_B$ for ESR. At room temperature and in 5 Tesla magnetic field, this corresponds to $10^{-5}$ for a typical NMR and $10^{-2}$ for ESR experiment. Only a very small fraction of spins available in a sample volume can be excited by applied microwave or RF field and detected even using the most sensitive detector. This fact explains why it is difficult to detect a spin resonance signal from a sample volume, which contains a small number of spins (since there are only one out of $10^5$ spins that will absorb net microwave power at room temperature). One method to get around this problem is optical pumping.

Optical pumping refers to the redistribution of atoms among their fine or hyperfine structure levels by means of light. This was first observed by J. Brossel, A. Kastler and J. Winter [J. Brossel, A. Kastler, J. Winter, J. Phys. Radium 13, 668 (1952)], following suggestions by A. Kastler [A. Kastler, J. Phys. Radium 11, 255 (1950)]. Optical pumping is usually performed with circularly polarized light. Just as light exerts radiation pressure, circularly polarized light can transfer angular momentum and produce a torque.

To understand the effect of optical pumping on the atoms, consider a simple experiment. FIG. 1 is a simplified energy-level diagram of a typical alkali metal. Consider an atom with a nucleus that has no nuclear spin and no magnetic momentum. In the ground state (or S state) the electron has no orbital angular momentum so that the angular momentum of the entire structure is solely the spin of the outer valence electron, which can be quantized in a direction parallel ($m_j=\frac{1}{2}$) or antiparallel ($m_j=-\frac{1}{2}$) to an external magnetic field. The circularly polarized light induces transitions from this S ground state to a P level, which has one unit of orbital angular momentum. Through the spin-orbit interaction, this level is split into two levels, for which the total angular momentum J is either 3/2 or 1/2, depending on the orientation of the electron spin with respect to its orbital motion. And in each level, 2J+1 sublevels are available, in which $m_j$ arranges from −J to J. The solid lines show the absorption process, which involves an increase of one unit of angular momentum when the atoms are irradiated with circularly polarized light along a selected axis. The dotted lines indicate the re-emission process, which can occur primarily by spontaneous emission and is therefore mostly unaffected by the absorbed light (although to some extent there are interesting interference effects between absorbed and emitted light).

After repeated fluorescence transitions of this kind, the atoms are stochastically shifted to occupy the higher quantum numbers m (or the lower ones, if the opposite direction of circular polarization is used) instead of following Boltzmann statistics. In the case of S-state atom with no nuclear spin, this is equivalent to saying that the valence electron is nearly 100% polarized, therefore dramatically increased the population difference in spin states.

Figure 2:
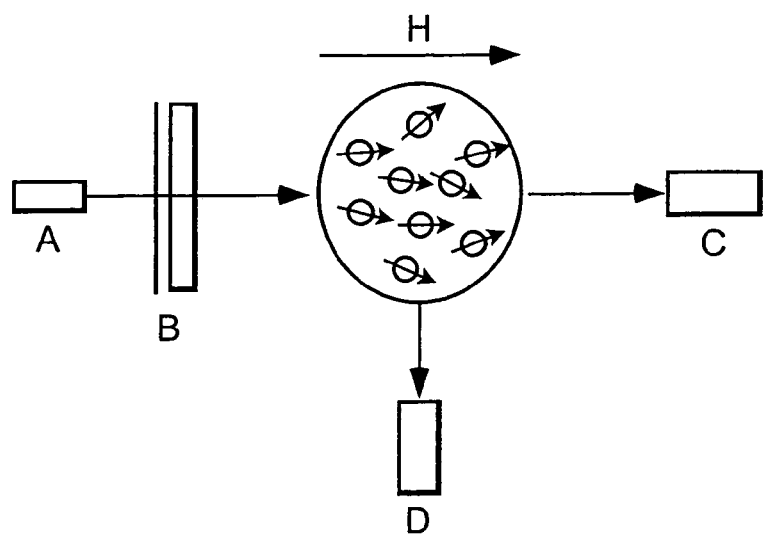
FIG. 2 schematically illustrates a simple optical pumping experiment, including a laser, a polarizer and quarter-wave plate, and one or more photodetectors.

Optical pumping also provides an optical detection mechanism for spin resonance in two ways, as illustrated in FIG. 2. When all atoms have been pumped into highest $m_j$ sublevel, the sample vapor will become transparent, and photodetector C will receive the full intensity of pumping light. Thus, observing the intensity of transmitted pumping light (transmission monitoring) is one important way to detect optical pumping. When complete optical pumping has occurred, there will no longer be any resonantly scattered light, and the intensity of fluorescent light at photodetector D will vanish. Consequently, pumping can also be detected by observing the fluorescent light through fluorescence monitoring.

If the nucleus of an atom used in optical pumping has a spin (denoted by a quantum number I) and a magnetic moment, in fields that are not too large, the magnetic moment of the nucleus will couple to the total angular momentum of the electron to form a new quantum number F, which ranges in unit steps of h between the sum of, and the difference between, J and I. In spite of the added complexity, optical pumping proceeds in exactly the same fashion as it does for the atom with electronic angular momentum only. It is therefore possible to do experiments with polarized nuclei (NMR) as well as with polarized electrons (ESR).

When combining optical pumping with the magnetic resonance technique, because an RF or microwave signal can induces hyperfine transitions of the atom in the magnetic field, which changes the electron distribution between the hyperfine levels, magnetic resonance will also have an effect on the optical pumping. Thus, optical pumping not only can enhance the population difference between hyperfine levels, which will enhance the sensitivity of magnetic resonance detection, it also can be used as a detector of magnetic resonance transition. However, this method cannot be applied for conventional bulk sample spin resonance experiments due to lack of optical access for optical pumping and detection (e.g. samples are usually inside a microwave cavity).

In 1990, D. Raftery et al [D. Raftery et al, Phys. Rev. Lett. 66, 584 (1991)] used laser pumping to enhance the pulsed NMR signal of $^{129}$Xe, allowing the detection of low-pressure xenon gas and of xenon adsorbed on powdered solids. The workers observed an increase in sensitivity of more than two orders of magnitude over conventional NMR.

Several groups have claimed to observe magnetic resonance spectroscopy of a single molecule spin with optical detection. The methods used by these groups were not the same as, but were similar to, a conventional optical pumping technique J. Kohler et al [J. Kohler et al, Science 268, 1457 (1995)] at the University of Leiden, Netherlands studied the individual pentacene-$d_{14}$ molecules doped into a p-terphenyl-$d_{14}$ host crystal by optically detected electron paramagnetic resonance spectroscopy. They mounted thin sublimation-grown crystals of p-terphenyl-$d_{14}$ containing about $10^{-8}$ mol of pentacene-$d_{14}$ per mol of p-terphenyl-$d_{14}$, which were cooled to 1.20° K between a LiF substrate and a quartz cover in the joint focus of a lens and a parabolic mirror. Even for these high quality crystals, the $S_1 \rightarrow S_0$ transition of pentacene is inhomogeneously broadened owing to the slight differences in the local environments of the guest molecules.

Exciting the system by a narrow band single-mode laser tuned far into the wing of this broadened transition, where the density of absorbers per unit frequency is very low, allows the detection of single molecules. The fluorescence emitted toward the red end of the absorption is collected by the parabolic mirror and recorded by photomultiplier and photon counting. When the molecule is excited into the $S_1$ singlet state, it can escape from the $S_0 \approx S_1$ excitation-emission cycle to the lowest triplet state $T_1$, with a probability of 0.5 percent. Consequently, the fluorescence photons are emitted in bunches with an average dark period that corresponds to the mean residence time of the molecule in the triplet state. The three sublevels of $T_1$, labeled $T_x$, $T_y$, and $T_z$, are selectively populated and depopulated by intersystem crossing. Because levels $T_x$ and $T_y$ have a short lifetime and a high population probability compared to level $T_z$, the mean residence time of a molecule in the triplet state is prolonged under the influence of a microwave (RF) field in resonance with the ($T_x$-$T_z$) or ($T_y$-$T_z$) transition. This allows the observation of these magnetic resonance transitions as a decrease in fluorescence signal (fluorescence-detected magnetic resonance (FDMR)). J. Wrachtrup et al [J. Wrachtrup et al, Nature 363, 244 (1993)] in Germany and France have performed a similar experiment for optical detection of magnetic resonance in a single molecule.

However, the optical technique does not have very high spatial resolution, which is limited by laser spot size. Although tapered optical fiber (near field optical probe) may give rise to better resolution in optical pumping, it will not be able to reach the power requirement of optical pumping due to waveguide decay problem.

Figure 3A:
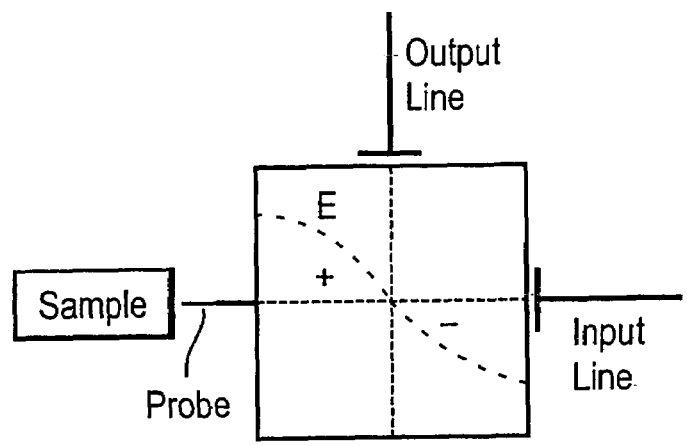
FIGS. 3A and 3B schematically illustrate an orthogonal mode microstrip resonator with a tip to generate an evanescent wave signal and tip shielding structure.
Figure 3B:
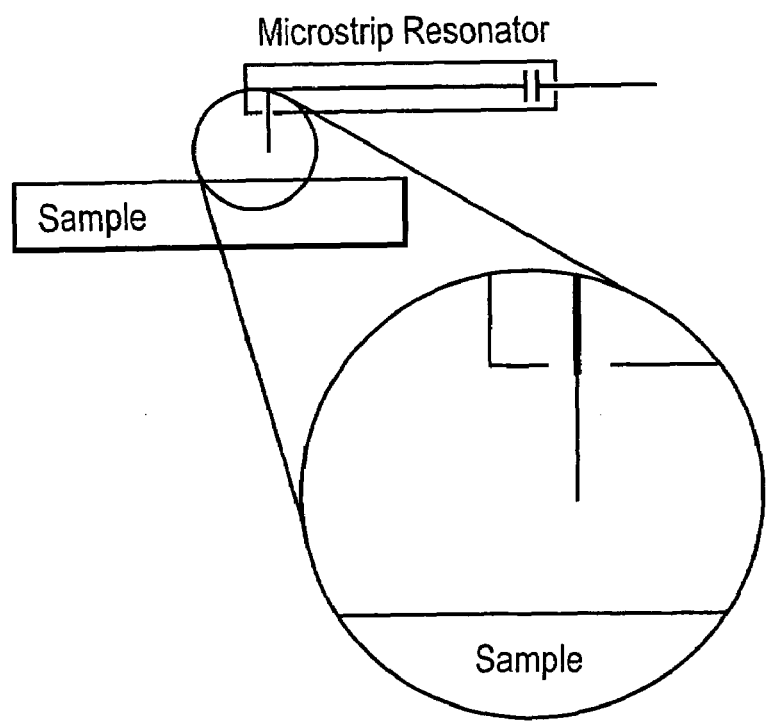

FIGS. 3A and 3B schematically illustrate one exemplary embodiment including a square microstrip resonator or signal coupler, which is open at all four edges, and an associated shield structure for a probe tip. Both input and output transmission lines are coupled to the center of resonator edges with capacitance coupling and at right angle with each other. A probe tip is attached to the opposite side of input line. Because the coupler is square, some of the resonant modes will be degenerate. The electric-field nodal line of one of the pair of lowest-frequency modes is illustrated and the direction of the electric field is shown in the figure. The resonance mode orthogonal to this mode will have a nodal line at horizontal direction. Note that the output microstrip transmission line will not couple to the illustrated mode since the end of the transmission line is an equal-potential surface and is situated symmetrically with respect to the nodal line. Viewed from another perspective, if the described mode is excited, it will not induce any net charge on the end of the output transmission line. However, it will couple to the input transmission line so that power can be fed in from the input line without any power being coupled out to the output line. Optionally, one or more parameters associated with the output line can be adjusted so that, if a sample is not excited, the magnitude of a signal appearing on the output line is minimized (preferably with zero minimum). The square resonator or signal coupler shown in 3A can be replaced by a circular resonator, or by another resonator shape (e.g., a regular octagon) that has at least one set of (two or more) degenerate orthogonal modes.

Figure 4A:
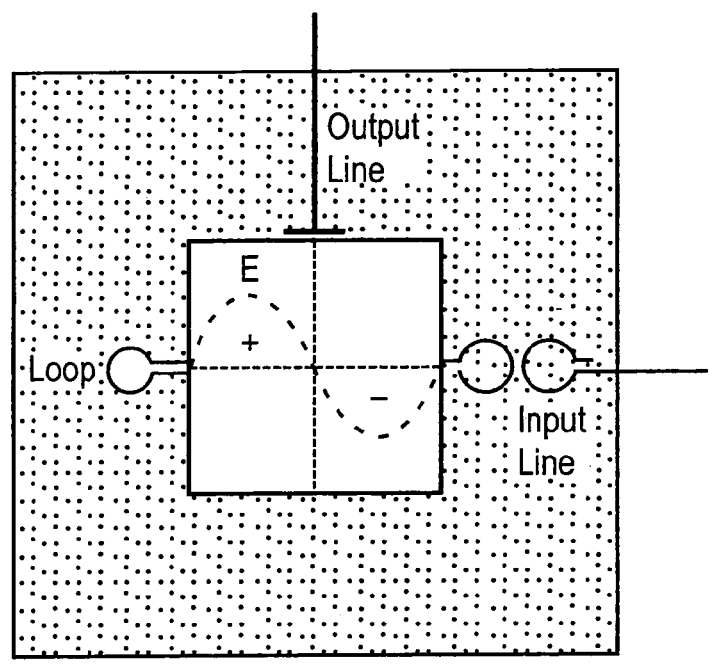
FIGS. 4A and 4B schematically illustrate an orthogonal mode microstrip resonator with loop tip to generate an evanescent wave and an associated shielding structure.
Figure 4B:
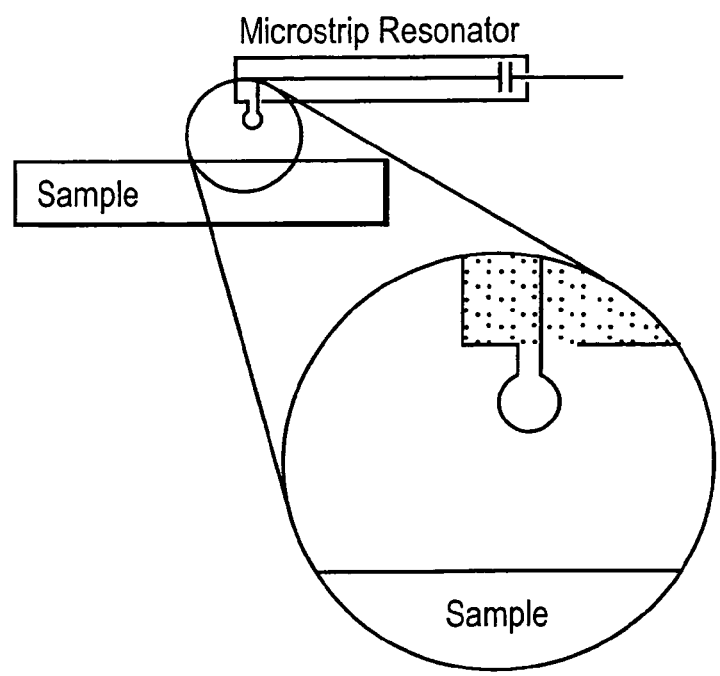

FIG. 4A illustrates a similar orthogonal resonator, where the evanescent wave probe is formed by a small metal loop connected between the center conductor edge and ground plane. When magnetic resonance is excited, this resonance destroys the symmetry of the driving mode, and some power is coupled to the orthogonal mode. As a consequence, the probe or tip will pick up the spin induction or absorption signal, which will be coupled out to the output transmission line and amplified by a low noise RF amplifier. A tip shielding structure for this microstrip resonator is shown in FIG. 4B.

In exemplary embodiments disclosed herein, such as those illustrated in FIGS. 3A, 3B, 4A and 4B, spin resonance of a spin of an atomic constituent can be detected in a time-continuous fashion wherein an excitation magnetic field is applied to a portion of a sample in a time-continuous manner (as opposed to a being applied in a pulsed manner) and wherein the spin resonance is detected using an evanescent wave probe located adjacent to the sample. Such spin-resonance detection is also referred to herein as a time-continuous mode.

In time-continuous mode embodiments, two cancellation schemes are available. In an external cancellation scheme, two substantially identical transmission line resonators (either a coaxial line, as shown schematically in FIG. 5 or a microstrip resonator or cavity/waveguide resonator) are used with one equipped with the evanescent probe (tip, loop or aperture as described herein) to generate an evanescent wave and interact with a sample. Optionally, each of two resonators is equipped with an evanescent probe, but only one probe is activated. In an external cancellation system 61, illustrated in FIG. 6, first and (phase shifted) second output signals from the first and second resonators, 62A and 62B, are received and processed by a summer or power combiner 65, for background signal cancellation, by an amplifier 67 and by a detector 69.

Figures 7A, 7B:
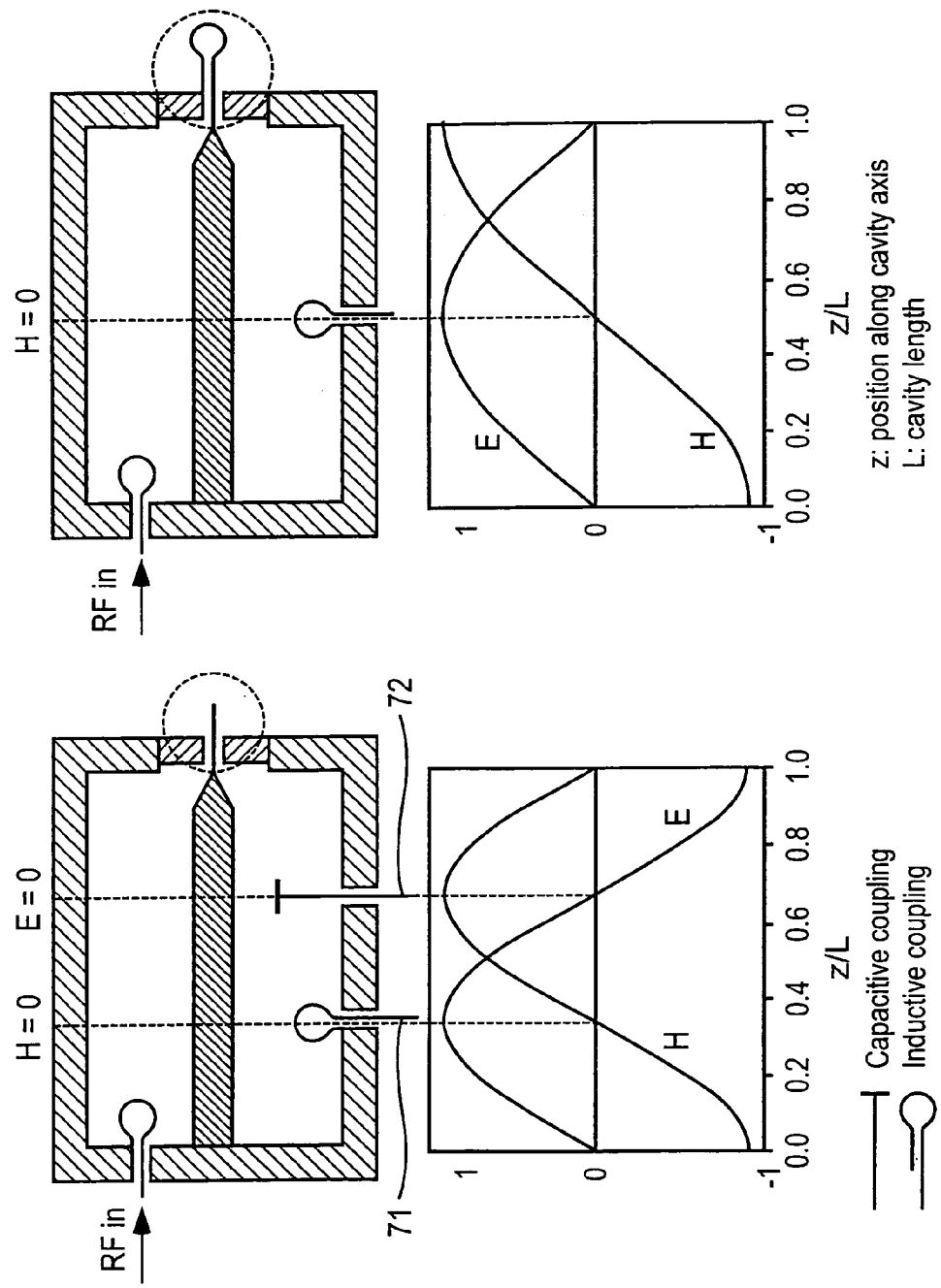
FIGS. 7 and 8 illustrate an internal cancellation scheme (transmission type and cavity type resonator, respectively), where the pickup coupling is positioned at the node of resonance mode of the resonator.
Figure 8:
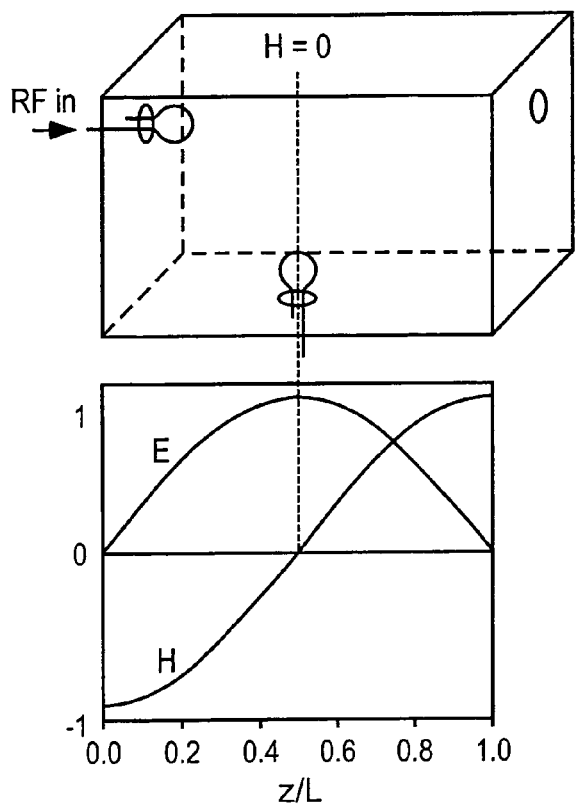

FIGS. 7A, 7B and 8 illustrate the optional internal cancellation schemes (capacitive coupling, inductive coupling and cavity resonator types, respectively) and the corresponding electrical and magnetic fields, where the pickup coupling is positioned at the node of resonance mode of the resonator. As the evanescent probe excites spin resonance, the node condition is broken and pickup coupling then detects the desired spin resonance signal. Here, the probe may be a small aperture in the housing. In the inductive coupling and capacitive coupling modes in FIG. 7A, the magnetic field H and electrical field E, respectively, vanish at the respective housing apertures, 71 and 72.

In another exemplary embodiment, illustrated in FIG. 7A, a node for a resonator or signal coupler is identified, where the signal vanishes or has a very small magnitude for a selected input frequency $f_{in}$ when no sample is present, for example the location marked "N," An output signal pickup module is then located at the node point N, and an input signal with the frequency $f_{in}$ is applied to the coupler to produce an evanescent signal at a sample located adjacent to the probe. A spin resonance response from the sample breaks the symmetry, and a relatively large output signal is then sensed at the node point, representing the spin resonance response of the sample.

Figure 9:
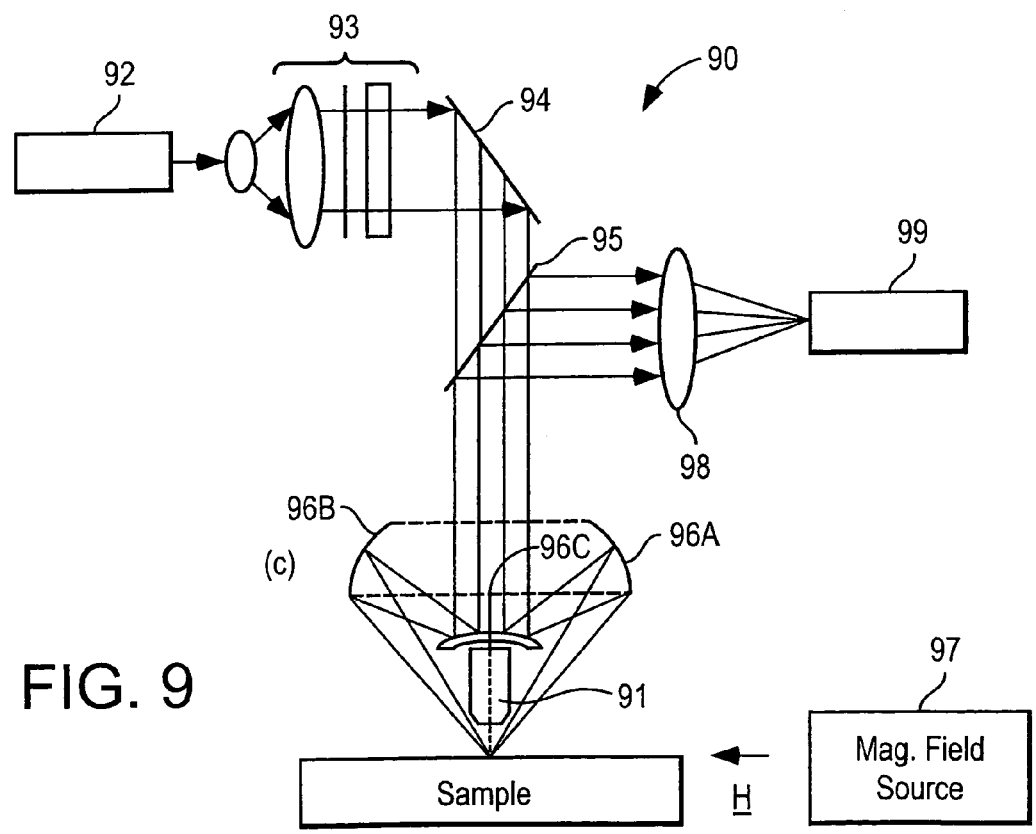
FIG. 9 schematically illustrates an optical pumping system, using a Schwartzschild optical objective, for use with an EMP approach.

In a further exemplary embodiment, fluorescence light is collected with the Schwarzschild optical objective and detected by a photodetector, as illustrated in the system 90 shown in FIG. 9. An evanescent microwave probe (EMP or evanescent wave probe) 91 is used to excite the spin resonance in one version.

A laser beam is generated at a light source 92 and is processed by a first optical system 93, optionally including a lens and/or quarter-wave plate and/or a first linear polarizer. The processed beam is reflected by a first reflector 94, passes through a partly transmissive second reflector 95, and is received by several optical components, 96A, 96B and 96C, of a Schwartzschild objective that directs the laser beam toward the sample. A magnetic field source (dc or slowly swept in field strength) 97 provides a field H that is generally perpendicular to the direction of the EMP signal. Light scattered or generated at the sample is redirected by the Scwartzschild objective components, is mostly reflected by the second reflector 95, is received and processed by a second optical system 98, optionally including a second linear polarizer-analyzer, and is received and analyzed by a detector 99. In a first operating mode, the EMP signal provides sample excitation and the laser beam provides sample interrogation and sensing. In a second operating mode, the roles of the two signals are partly reversed.

By measuring the change of intensity or polarization of fluorescence light produced by the laser beam, one can obtain a spin resonance signal. Optical detection has very high sensitivity, which may allow one to achieve single spin detection. In order to achieve this high sensitivity, the cancellation of transmitted pumping light background is necessary. Transmitted light is usually circularly polarized, while the fluorescence light is usually linear polarized. A quarter-wave plate can be used to transform the circularly polarized transmitted light to linear polarized light, which is oriented at a right angle to the polarized direction of fluorescence light. In this case, a linear polarizer can be used to block the transmitted light and allow the fluorescence light to pass.

In a transmission type resonator with an evanescent wave probe, a shielding wall with an aperture, from which the probe (metal tip or loop) extends from the resonator and interacts with the sample, can be used to increase the spatial resolution.

Figure 10:
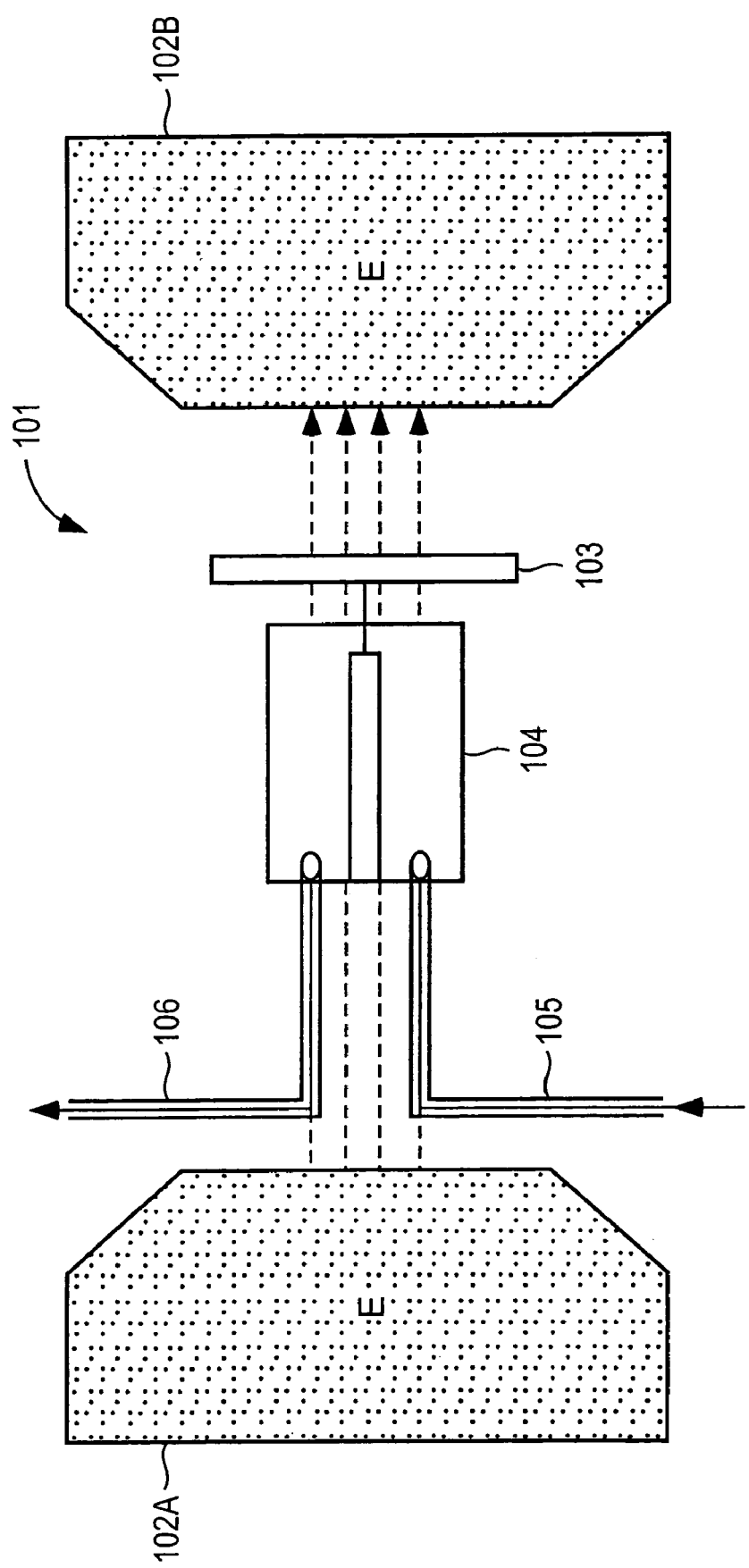
FIG. 10 schematically illustrates use of EMP apparatus for magnetic resonance detection.

An embodiment of an experimental set-up 101 is illustrated in FIG. 10. Two spaced apart electromagnet poles, 102A and 102B, have a sample 103 positioned between them. An EMP probe 104, located adjacent to the sample 103, is fed by an RF signal source 105 and transmits evanescent waves to the sample. Spin resonance signals are detected by the EMP probe 104 and are transmitted by an RF signal output module to a suitable detector-analyzer.

A measurement of ferromagnetic resonance (FMR) of a YIG single crystal was conducted using an Evanescent Microwave Probe. The sample is a YIG single-crystal with a dimension of 4 mm×4 mm×0.5 mm. The electromagnet has a 1.5" gap between a pair of 3" diameter poles. The shape of the poles was designed to have a magnetic field uniformity of about $10^{-5}$ in a 1 cubic inch sample volume at the center of the gap.

In the FIG. 10 example, the measurements were made by attaching the sample to an EMP tip. The EMP resonator serves as a spin resonance excitation RF source as well as a detector. EMP microwave electronic and digital acquisition system measures the changes in cavity resonant frequency and quality factor Q while scanning the external magnetic field. When a ferromagnetic resonance condition is satisfied, a sample volume near the EMP tip will interact with EMP. This condition was detected by measuring resonant frequency $f_r$ and quality factor Q of the EMP resonator.

Figure 5:
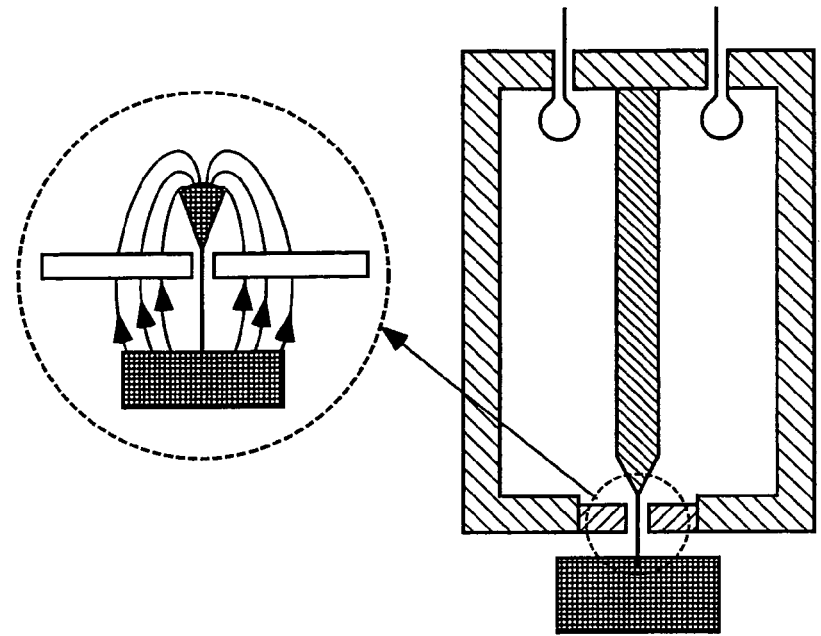
FIG. 5 schematically illustrates EMP apparatus.
Figure 6:
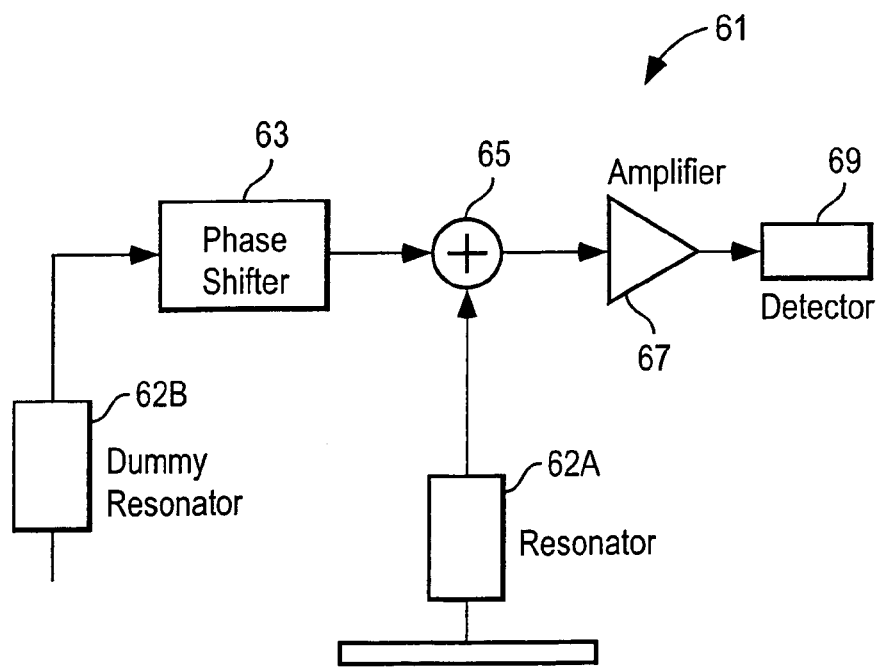
FIG. 6 schematically illustrates an external cancellation approach.

The EMP can be made of a λ/4 transmission line resonator, as illustrated in FIG. 5 (a coaxial resonator or a microstrip resonator are two examples) with an electrically conducting tip connected to the central conductor or a loop connected between the center conductor and ground shielding, or cavity type resonator with an aperture type evanescent probe. To achieve better spatial resolution, the end-wall of the resonator can be shielded by a thin metal film with an aperture in transmission type resonator cases. A tip or loop for the probe extends beyond the shielding wall from the aperture. An EMP tip is used to provide microwave radiation and define the spatial resolution.

A variety of evanescent wave probes (also called herein EWP) can be included in the spatially resolved spin resonance spectroscopy systems, apparatus, and methods disclosed herein. For example, the evanescent wave probe can be an evanescent microwave probe (also called herein EMP) or any other type of evanescent wave probe operating in a different wavelength region, e.g., radio frequencies (RF). Various embodiments disclosed herein are described as using an EMP, but it should be understood that an evanescent wave probe of any frequency can be used. Some of the example evanescent wave probes are shown in FIGS. 7A to 7B and FIGS. 11 to 14B.

FIG. 11 schematically illustrates an evanescent wave probe 110. A center conductor 112 extends at a distal end beyond a small aperture 114 in the shielding end-wall 116 and forms a tip 118. Depending on the length of the outside portion 120 of the tip 118, the oscillating current flowing along the tip 118 will produce RF radiation to a scale much larger than the size of tip 118, which will decrease the EMP space resolution. To reduce the far-field radiation effect, a grounded metal wire 122 is connected to the cavity shielding 124 and placed adjacent to the center conductor 112 at the outside portion 120 of the tip 118. The construction of the evanescent wave probe 110 limits the electromagnetic field effectively between the tip 118 and the ground wire 122 and increases the space resolution dramatically. The evanescent wave probe 110 also optionally includes a first loop 126 on an end-wall and a second loop 128 on an end-wall. The end-wall can be any end-wall, such as second end-wall 130 opposite end-wall 116. The first loop 126 and second loop 128 can each, independently and optionally, be connected to a source for electromagnetic energy, such as a RF generator (shown in FIG. 16), or a detector for electromagnetic energy, such as a RF detector (shown in FIGS. 16 and 17). The loop 126 and 128 (and corresponding features illustrated in FIGS. 12 and 13) provide for inductive coupling of electromagnetic radiation, e.g., RF, Microwave and other, into and out of the evanescent wave probe 110. Optional, one or more of the loops 126 and 128 can be replaced with capacitive elements or with direct electrical connections to capacatively or directly couple electromagnetic radiation into and out of the evanescent wave probe 110.

When only connected to a detector for electromagnetic energy, the evanescent wave probe 110 operates in a passive mode to detect a signal. When connected to a source for electromagnetic energy, the evanescent wave probe 110 operates in an active mode to further generate an evanescent wave.

Similar to the structure in FIG. 11, FIG. 12 schematically illustrates an evanescent wave probe 140. In this exemplary embodiment, instead of a grounded wire, the outside part of the tip 134 of the center conductor 132 is surrounded by low loss insulating material 136, and then coated with a layer of conductive film 138, which is electrically connected with the cavity shielding at, for example, end-wall 140. The illustrated structure in FIG. 12 substantially eliminates the far-field RF radiation and has better resolution than a two wire structure.

The tip of the evanescent wave probe cavity can optionally be replaced with a conductive loop 152 as shown in the exemplary embodiment 150 of FIG. 13. One side 154 of the conductive loop 152 is connected to the center conductor 156 and another side 158 is connected to the cavity shielding 160, at, for example, end-wall 162. The conductive loop 152 extends beyond an aperture 164. The aperture can be at a thinned metal shielding portion of end-wall 162 and connects back to the end-wall 162 to form a λ/2 resonator.

In exemplary embodiments, the conductive loop 152 can be either a single-loop structure or a multiple-loop coil. Also, the evanescent wave probe can be used for NMR/ESR signal excitation and detection. The oscillating magnetic field inside the sample produced by the one or more conductive loops is in a horizontal direction, which is perpendicular with the external static magnetic field.

Because the current flowing in the two wires connecting the loop is in opposite direction with each other, the RF radiation emitted by these two wires will effectively cancel each other to a very low level. Thus, only the portion of the sample immediately under the loop will be sensed. Compared to the tip structure in FIGS. 11 and 12, the loop probe in FIG. 13 is much more sensitive to magnetic signal, but has a lower resolution.

The schematically illustrated exemplary loop structure can also be used in transmission line type probes, such as the exemplary transmission line 170 illustrated in FIG. 14A or transmission line 190 illustrated in FIG. 14B. The transmission lines 170, 190 include two conductive lines 176, 178 and 196, 198. Optionally, a dielectric insulating material 179, 199 can be placed between and/or around such conductive lines. Transmission line 170 can also include a further shield electrode 180 connected, for example, to ground. The front end 172, 192 of the transmission line 170, 190 is optionally tapered down to increase spatial resolution, and a conductive loop 174, 194 is attached thereto. The tapered region of the transmission line is at a distal end of the structure, such as a distal end from a housing, a mounting surface, a control surface, or a clamping structure supporting and/or manipulating the transmission line. In one exemplary embodiment, the transmission line is substantially configured as a coaxial cable. For coaxial cable, the loop is connected to the center conductor and outside shielding layer. For the structure in FIG. 14B, the loop is connected to the two conductive lines. The examples illustrated in FIGS. 14A and 14B each include two conductive lines 170A, 170B and 190A, 190B. However, multiple pairs of conductive lines can be used in each exemplary embodiment, e.g., four conductive lines in each exemplary embodiment, each pair of lines optionally having a conductive loop.

Figure 15A:
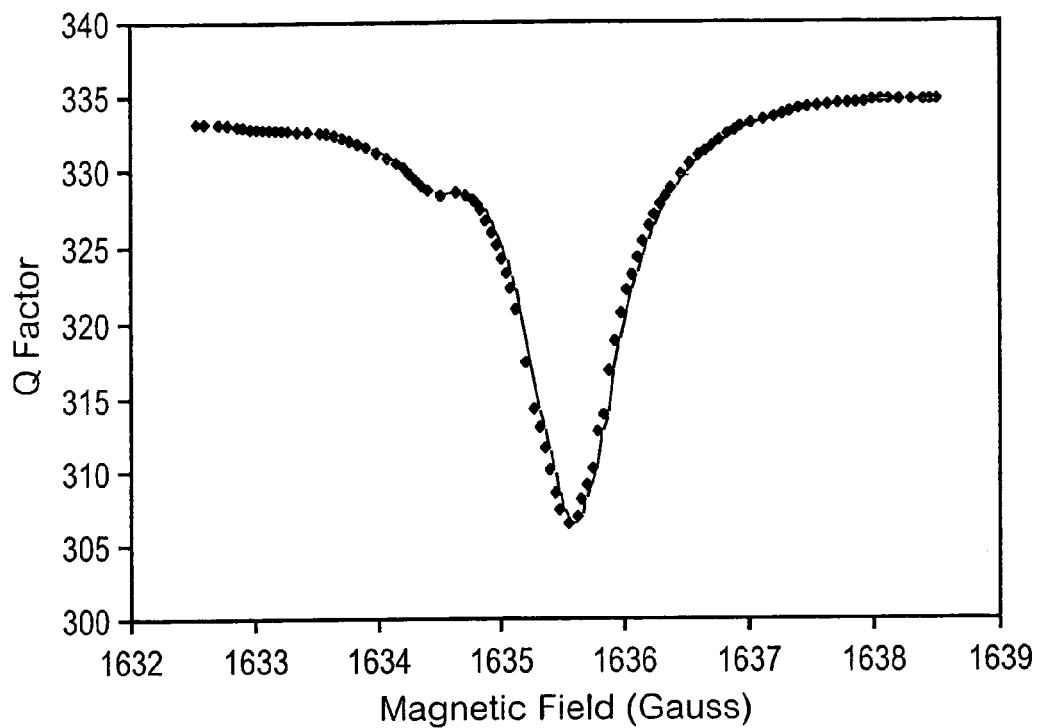
FIGS. 15A and 15B graphically EMP resonance and Q factor versus magnetic field strength H for a YIG sample.
Figure 15B:
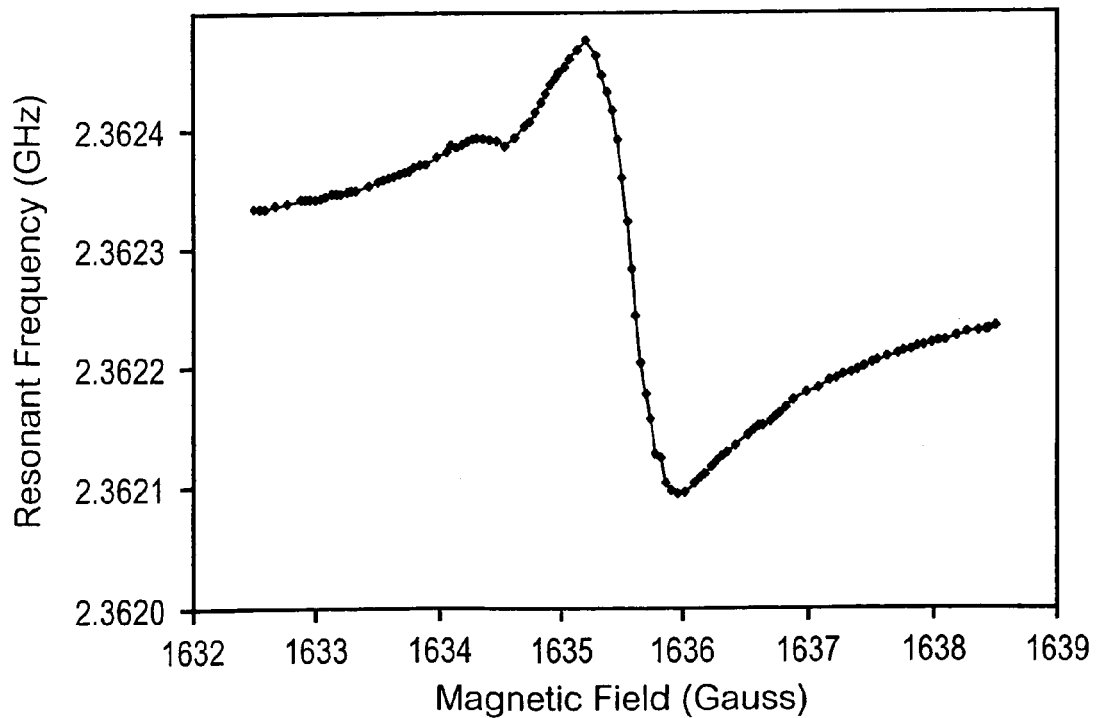

FIGS. 15A and 15B graphically illustrate FMR curves obtained by measuring the EMP resonant frequency and Q versus external magnetic field H using an evanescent wave probe. The relation between $f_r$ and H arises from changes in the propagation constant of the probe circuit that are caused by a dispersion influence of the real part of the permeability μ', according to a relation $$\mu' = 1 + \frac{\gamma 4\pi M(f - f_0)}{(f^2 - f_0^2) + \gamma^2(\Delta H)^2} \quad (2)$$

$$\approx 1 + \frac{\gamma 4\pi M(f - f_0)}{\gamma^2(\Delta H)^2} \text{(near resonance)}$$

where $f_0$ is the FMR frequency and $\gamma(=2.8 \text{ GHz/kOe})$ is the gyromagnetic constant. Absorption of microwave energy will reduce the Q factor of the probe through the resonance peak in the imaginary component $\mu''$, according to $$\mu'' = \frac{\gamma 4\pi M \gamma(\Delta H)}{(f^2 - f_0^2) + \gamma^2(\Delta H)^2} \quad (3)$$

$$\approx \frac{\gamma 4\pi M}{\gamma(\Delta H)} \text{(at resonance)}$$

The actual FMR condition is established when the proper Kittel relation is satisfied. In this experimental configuration, $$f_0 = \gamma\sqrt{H(H + H_K + 4\pi M)}, \quad (4)$$

where $H_K$ is the anisotropy field ($\approx 50$ Oe) that is usually ignored when approximate values are sufficient.

In another embodiment, high spatial resolution, high contrast topography and high sensitivity spin magnetic resonance spectroscopy are simultaneously achieved using a pulsed NMR technique with an evanescent microwave probe (EMP), integrated with an atomic force detection sensor.

An evanescent microwave probe (EMP), a highly sensitive microwave detection technology as previously described and illustrated herein, operates by sending evanescent microwave and detecting its interaction with the sample through a conducting tip. Evanescent wave differs from the far-field wave in that it does not radiate or propagate in space, but is localized only near the surface of a sharp conducting tip. Evanescent wave has a much higher spatial resolution than the propagating microwaves or RF waves ($\sim\lambda$).

The conducting tip has a radius much less than the microwave wavelength ($\lambda$) connected to a microwave resonator. This interaction depends on complex electrical impedance (including both the real and the imaginary parts) of the sample. The interaction causes a change in resonant frequency ($f_r$) and quality factor (Q) of the resonator. The EMP can simultaneously measure the real and imaginary part of the sample's electrical impedance as well as the surface topography by detecting the shift in resonance frequency and quality factor of the sensing resonant probe The EMP obtains relatively pure evanescent microwave near the tip while at the same time maintaining a very high quality factor (Q) of the microwave sensor (resonator). The probe is based on a high Q resonator, e.g., microwave coaxial resonator, with a sharpened metal tip mounted on a center conductor. Since the tip is an integral part of a sensitive detector (microwave resonator with Q of a few thousands), the sensitivity of the instrument can be very high. The tip extends beyond an aperture formed on a thin metal shielding end-wall of the resonator. The tip and the shielding structure are designed so that the propagating far-field components are shielded within the cavity whereas the non-propagating evanescent waves are generated at the tip. Only when the tip is in close proximity of the sample will the evanescent waves on the tip interact with the materials. Both theoretical and experimental analysis indicate that the EMP tip picks up signals from a small volume proportional to (tip radius)$^3$. Sub-micron spatial resolution has been realized with tip radius on the order of one micron.

Conventional NMR/ESR measurements suffer limited spin sensitivity due to a large power signal background, which will decrease the instrument's ultimate sensitivity dramatically. To reach the intrinsic sensitivity, the background signal should be decreased to as low as possible without sacrificing the excitation power. To move toward a zero background limit, a pulsed detection configuration (e.g., a time-resolved detection configuration) can be utilized in exemplary embodiments. The basic idea of the pulsed technique is to apply a certain time of RF excitation signal to the sample, and to detect the emitted RF signal from the sample after the pulse. Since the detection and excitation do not occur at the same time, there is no background power coupling from the excitation signal. What is detected comes substantially purely from the spin resonance of the sample. Therefore, a true zero background signal detection limit can be approached and the intrinsic high sensitivity achieved.

Figure 16:
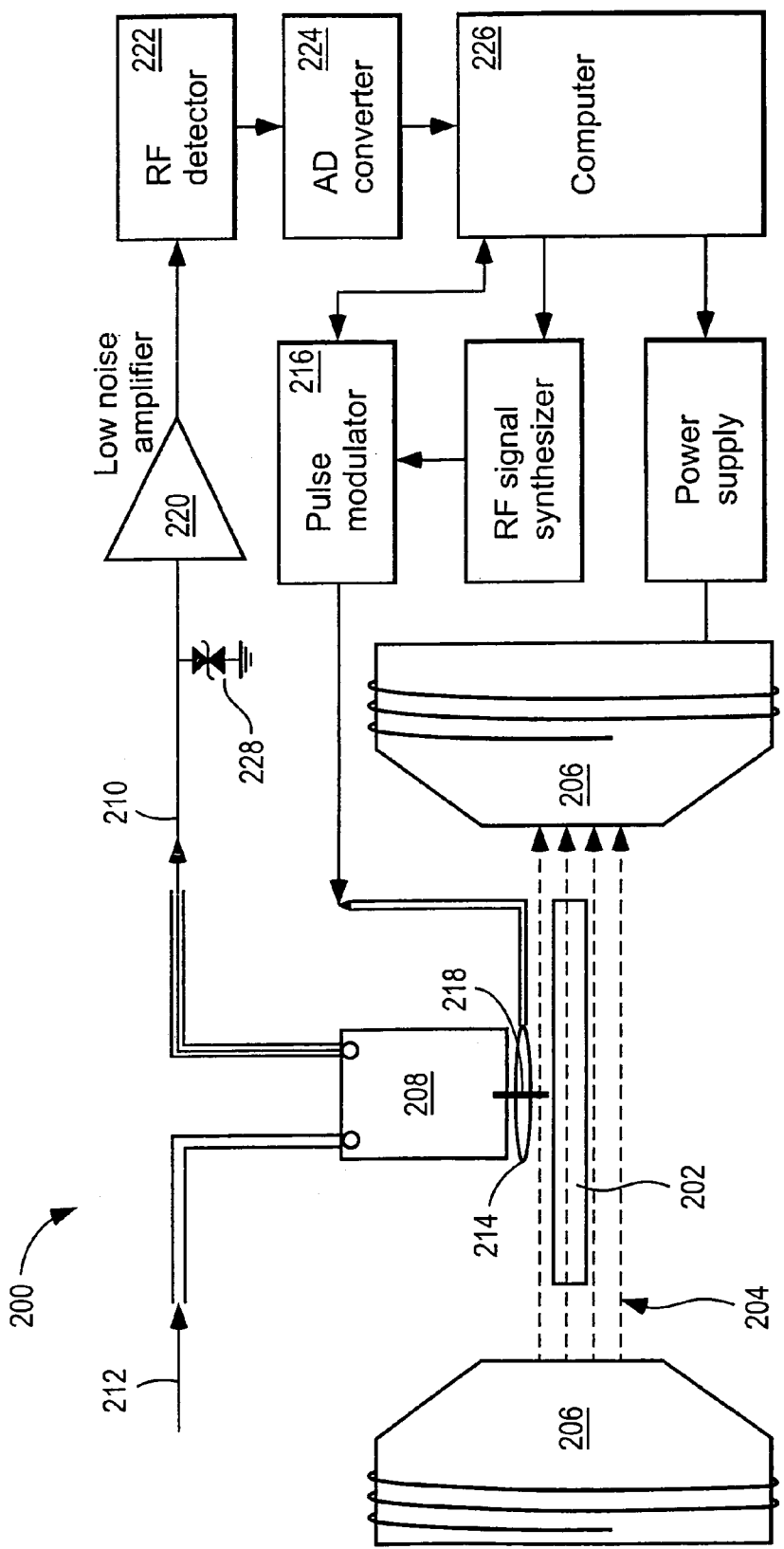
FIG. 16 is a schematic illustration of an exemplary embodiment of an apparatus for spatially resolved spin resonance spectroscopy.

In one exemplary device configuration 200 illustrated in FIG. 16, the sample (with scanning stage 202) is placed in a uniform magnetic field 204 generated by electromagnet 206. A RF resonator 208 (such as a helical resonator for NMR measurement or a coaxial resonator for ESR measurement) can be used as a passive sensor to detect spin resonance (corresponding to output signal 210), in which case a small orthogonal RF coil 214 is controlled by the pulse modulator 216 to apply an intense RF excitation pulse to the sample. Optionally, the RF resonator 208 can be used as an active sensor by supplying excitation energy 212 to the RF resonator 208 to excite the sample, the RF resonator 208 also being used as the spin-resonance sensor. The RF resonator 208 is placed just above the RF coil 214 with its metal tip 218, e.g., a distal end of a tip of an evanescent wave probe, going through the RF coil 214 center. The frequency of the RF excitation signal will be tuned to the same or close to (e.g., within a bandwidth) of the resonant frequency of the RF resonator 208. For simplicity, the quartz tuning fork mounted on the RF resonator is not drawn here.

Typical experiments begin with the net nuclear spin magnetization $\overline{M}$ aligned along the magnetic field direction. During measurement, a certain width of the RF pulse will be applied to the sample under the RF coil so that the nuclear (or electron) spins of the sample will rotate 90° from their original direction and align in a direction perpendicular to the magnetic field. The magnitude of the applied RF magnetic field $H_1$ and the applied pulse time width $t_w$ have to satisfy the following relationship to achieve the 90° spin rotation, $$\gamma H_1 t_w = \frac{\pi}{2}, \quad (5)$$

where $\gamma$ is the gyromagnetic ratio of nuclear (or electron) spin.

After cessation of the pulse, the 90° bended spins will start to precess around the axis of magnetic field direction. This precessing induced RF emission will be picked up by the RF resonator 208 through tip coupling, amplified by a low noise RF amplifier 220 and finally detected by a RF detector 222. The detected signal will be converted to a digital signal by an AD converter 224 and processed by a computer 226. A Zener diode 228 is used in front of the low noise amplifier 222 to limit the input RF power caused by the RF pulse and for protection.

In the exemplary embodiment illustrated in FIG. 16, a time-resolved and spatially resolved measurement of impedance in a sample can also be made, either alone or in conjunction with a spin-resonance measurement as discussed above. In such a time-resolved impedance measurement, the RF resonator 208, or any suitable evanescent wave probe as described herein, is positioned adjacent to a sample. Such an evanescent wave probe is configured to generate an evanescent wave including at least one of a time varying amplitude and a time varying phase. A detection circuit, such as RF detector 222, detects a time-resolved change in a resonance frequency of the evanescent wave probe and a time-resolved change in a quality factor of the evanescent wave probe. A processing system, such as computer 226, processes the change in the resonance frequency and the change in a quality factor to produce an impedance measurement using suitable algorithms, such as described in U.S. Pat. Nos. 5,821,410 and 6,532,806, the entire contents of which are incorporated herein by reference.

Figure 17:
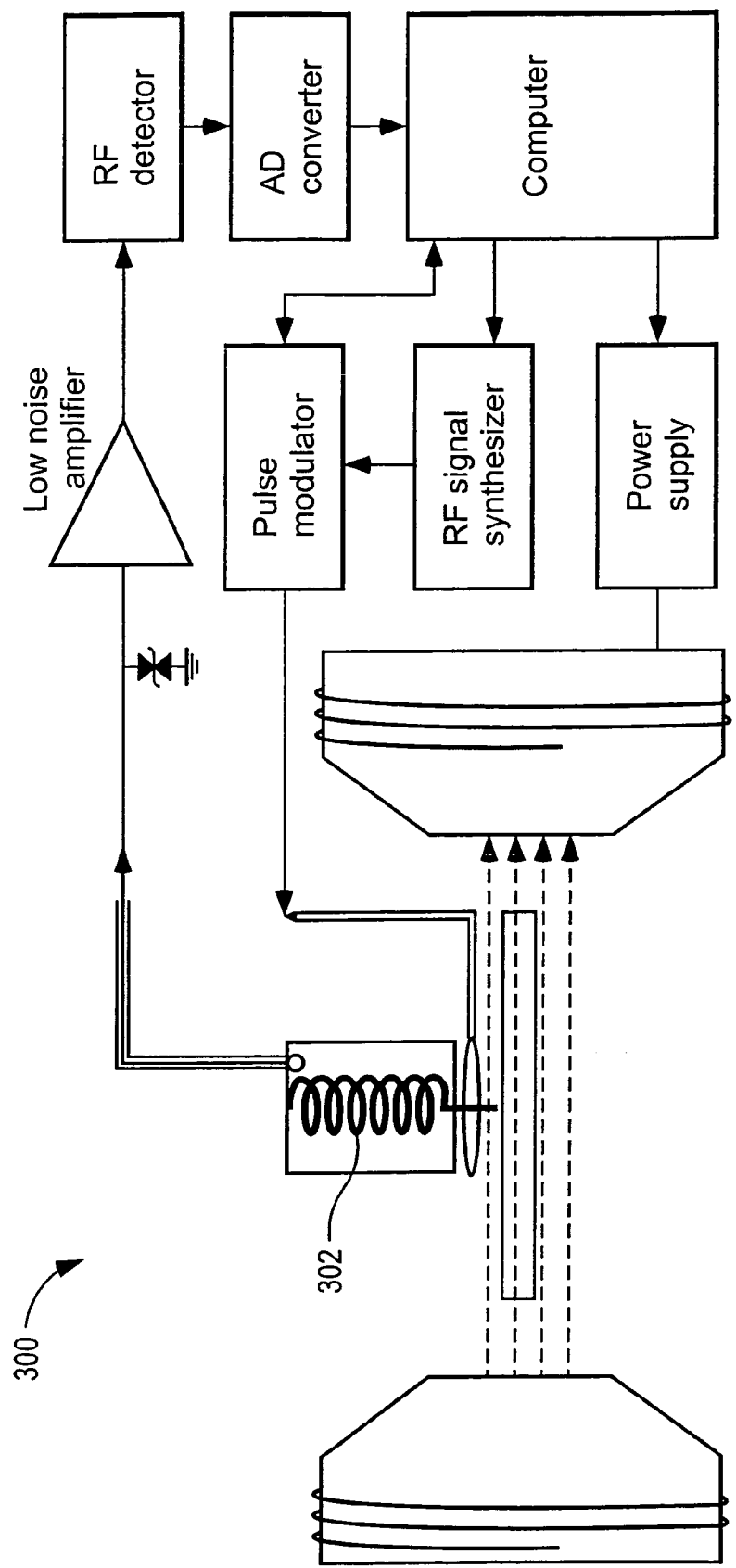
FIG. 17 is a schematic illustration of another exemplary embodiment of an apparatus for spatially resolved spin resonance spectroscopy where the evanescent wave probe includes a helical coil.

FIG. 17 is a schematic illustration of another exemplary embodiment of an apparatus for spatially resolved spin resonance spectroscopy where the evanescent wave probe includes a helical coil. The FIG. 17 exemplary embodiment 300 is similar to the embodiment 200 described with respect to FIG. 16. In FIG. 17, the RF resonator is illustrated with a helical coil 302. Also, the embodiment 300 is illustrated as an optional passive device because no input, analogous to input 212 of FIG. 16, is supplied to the RF resonator.

In addition to a time-continuous mode of spin-resonance detection, such as described above, exemplary embodiments can employ a time-resolved mode of spin-resonance detection such as when a pulse of magnetic energy is applied to a portion of a sample, and a spin-resonance measurement is made subsequent to the pulse.

In a time-resolved mode of detection, a time-resolved measurement of at least one property of the spin resonance can be made using the evanescent wave probe (or other type of probe such as described herein). Exemplary properties include a resonant frequency and a time decay, e.g., a relaxation time. In a time-resolved mode, a detected spin processing signal will start to decay after an applied pulse is removed/completed due to the spin-spin and spin-lattice interaction inside the sample. This is the spin relaxation time. Due to near field effect, the RF resonator tip 218 only picks up the emitted signal coming from a very small volume of the sample in the proximity of the tip 218, which has a dimension of about 1 mm$^3$ to 10$^3$ nm$^3$. By scanning the sample, a high spatial resolution spin resonance image of the sample can be obtained.

The image contrast comes from the different intensity or line width of spin resonances, or chemical shift of the nucleus in sample molecules. For NMR, chemical shift actually means the spin resonance frequency difference between different nucleus or different molecules in different locations. When the experiment is operated in one fixed RF frequency, some parts of a sample will have spin resonance and some parts will not have spin resonance or will have a weak spin resonance because of the chemical shift. As a result of this difference, a difference or contrast will appear in the detected spin resonance data.

In addition, in time-resolved mode the evanescent wave probe can be replaced in the exemplary embodiments disclosed herein by a miniature magnetic sensor to conduct time-resolved NMR. The miniature magnetic sensor can be any suitable magnetic sensor sized to sense a sample volume having an order of magnitude of about 1 mm$^3$ to 10$^3$ nm$^3$. Examples of minicoils and microcoils suitable for adaptation for use as the miniature magnetic sensor are disclosed in U.S. Pat. No. 6,097,188, the entire contents of which are incorporated herein by reference.

Figure 18:
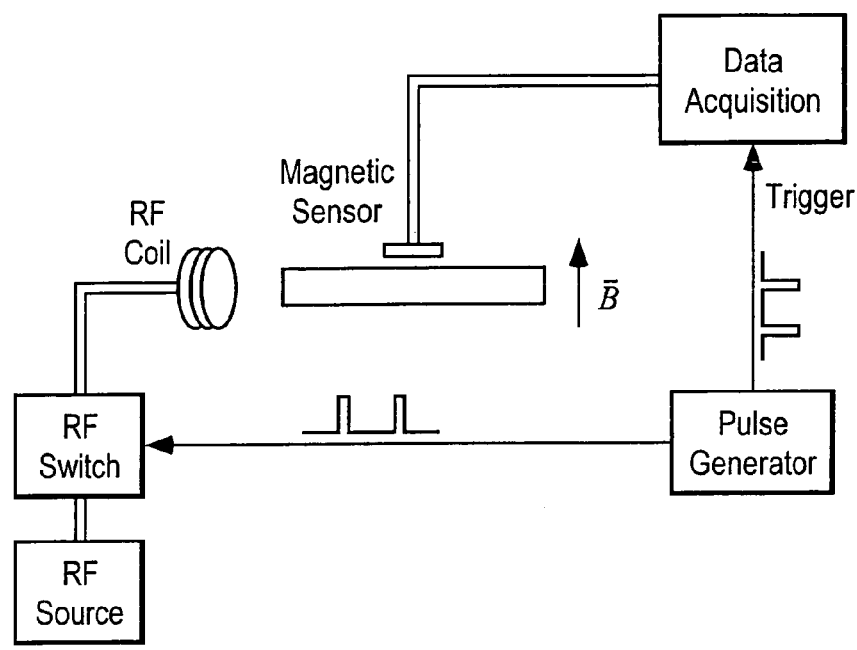
FIG. 18 is a schematic illustration of another exemplary embodiment for spatially resolved spin resonance spectroscopy using a miniature magnetic sensor.

Various other kinds of magnetic sensors, such as tunneling magnetoresistance sensors (TMR), giant magnetoresistance sensors (GMR), Hall devices, or magneto-restrictive sensors, can also be used as a miniature magnetic sensor, instead of an evanescent wave probe, for carrying out time-resolved spin-resonance detection as described herein. As illustrated in FIG. 18, a miniature magnetic sensor is used to detect the magnetic signal induced by spin resonance, while a RF coil is placed close to the sample to provide RF excitation signal. The oscillating magnetic field produced by the RF coil is perpendicular to the external magnetic field $\vec{B}$.

The real part of the susceptibility near spin resonance has the following relationship with RF frequency $\omega$ (or magnetic field H), $$\mu' = 1 + \frac{\gamma 4\pi M(\omega - \omega_0)}{(\omega^2 - \omega_0^2) + \gamma^2(\Delta H)^2} \quad (6)$$

$$\approx 1 + \frac{\gamma 4\pi M(\omega - \omega_0)}{\gamma^2(\Delta H)^2} \text{(near resonance)}$$

By measuring the susceptibility of the sample, magnetic sensor can be used to detect spin resonance. The time-resolved measurement is achieved by modulating the RF coil signal with a RF switch and a pulse generator, and in the mean time, measuring the spin resonance signal decay with pulse synchronized data acquisition.

In further exemplary embodiments, independent tip-sample distance control can be integrated into any of the exemplary embodiments disclosed herein, e.g., the spin resonance system and/or the impedance system, for magnetic resonance detection. For example, tip-sample distance control can be provided by a scanning probe microscope (SPM). The sensitivity of SPM is a function of tip-sample distance. Since the EMP tip will sense the magnetic resonance induced induction and absorption, a known tip-sample distance during magnetic resonance detection contributes to precise interpretation of the detected signal. Additionally, when a highly conductive sample is measured tip contact with the surface greatly reduces the Q, which determines the sensitivity.

In one exemplary embodiment, SPM in the form of atomic force microscopy (AFM) is integrated with the spin resonance and/or impedance systems to control probe sample distance. The EMP can utilize such control to realize its powerful capacities for microwave impedance detection.

Atomic force is known to have strong dependence on tip-sample distance and has been widely used to image surface topology of various samples. Exemplary embodiments integrate a commercial quartz tuning fork cantilever with the EMP system as a tip-sample distance control mechanism by detecting the atomic force between the tip and the sample. The quartz tuning fork base is fixed rigidly on the resonator cavity, and the EMP tip is attached to one of the tuning fork arms using an adhesive. During measurement, the tuning fork is driven by an AC signal synthesizer with a frequency the same as or close to the resonant frequency of the tuning fork. The tuning fork's vibration signal is read by using a detection circuit. The variation of atomic force between the EMP tip and measured sample (i.e., the tip-sample distance change) will dramatically change the resonant frequency and quality factor of the tuning fork. Therefore, the tuning fork signal can be used to measure the sample's topography and to regulate the EMP tip-sample distance.

There are many ways to realize the atomic force detection, some of which are summarized in Table 1. There are basically three atomic force modes, one is a DC mode and two are AC modes. The DC mode is also called the contact mode. The direct contact between probe and sample will cause the mechanical bending of the probe, which can be detected by the listed detection methods in Table 1. The AC mode detects mechanical vibration of the probe, which is usually equal to or close to the mechanical resonant frequency. When the tip closes to the sample surface, the atomic force will change the vibration properties which can be detected by the listed detection method in Table 1. The AC mode can be either a tapping (normal) mode or a shear force mode. In tapping mode, the probe vibrates substantially perpendicular to the sample surface at the contact point. In shear force mode, the probe vibrates substantially parallel to the sample surface.

TABLE 1

Methods of atomic force detection in SPM applications

| Detection Method | | Atomic Force | | |
|---|---|---|---|---|
| | | DC contact | AC tapping | AC shear force |
| Optical detection | Reflection beam | X | X | X |
| | Interference detection | X | X | X |
| | Diffraction beam | N/A | N/A | X |
| Non-optical detection | Electron tunneling current | X | X | X |
| | Tuning fork | N/A | X | X |
| | Other piezo-electric device | X | X | X |
| | Piezo-resistive device | X | X | X |
| | Microwave | X | X | X |

X = combination present

To detect the atomic force induced mechanical changes like bending or vibrating properties, several methods have been developed. These methods can be separated into two categories—optical detection and non-optical detection. The different methods in each category are listed in Table 1 and summarized below.

Exemplary Optical Detection Methods.

Figure 19:
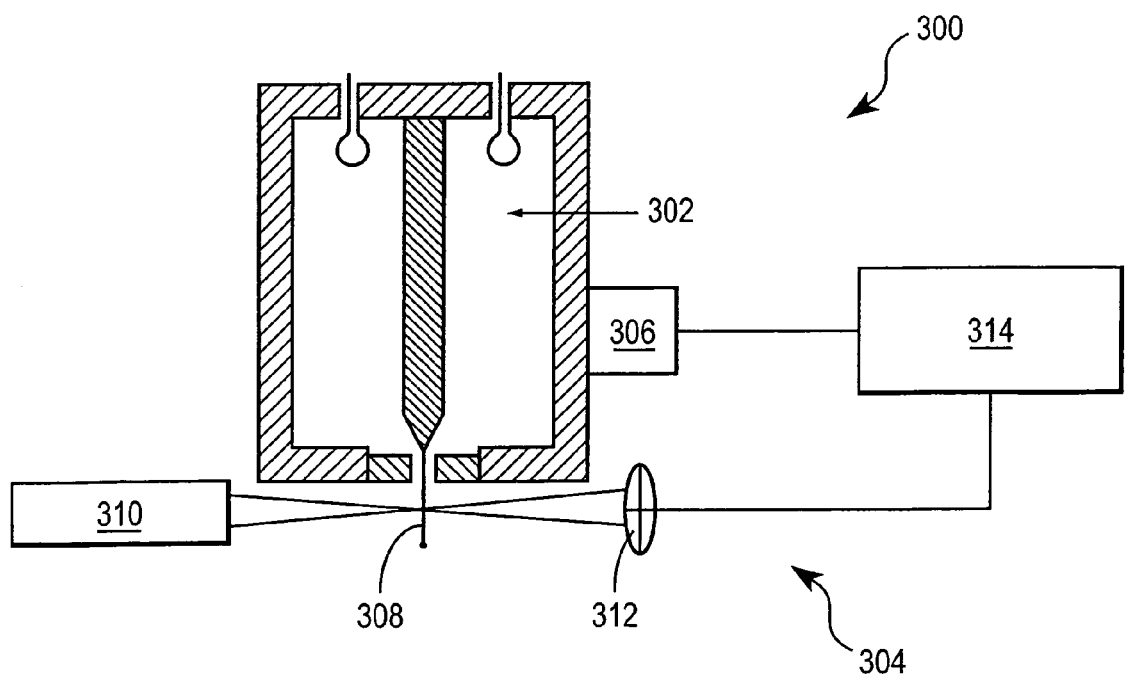
FIG. 19 schematically illustrates an exemplary embodiment of an evanescent wave probe integrated with a scanning probe microscope.

Reflection beam detection: The laser beam is focused on the probe and reflected by the mirror like structure near the end of the probe. The bending or vibration of the probe will cause the change of direction of the reflected laser beam, which can be detected by position sensitive photo diode (PSPD). A PSPD is a square or circle photo diode evenly split in to 2 or 4 independent sections. An example is illustrated in FIG. 19, discussed further below.

Figure 20:
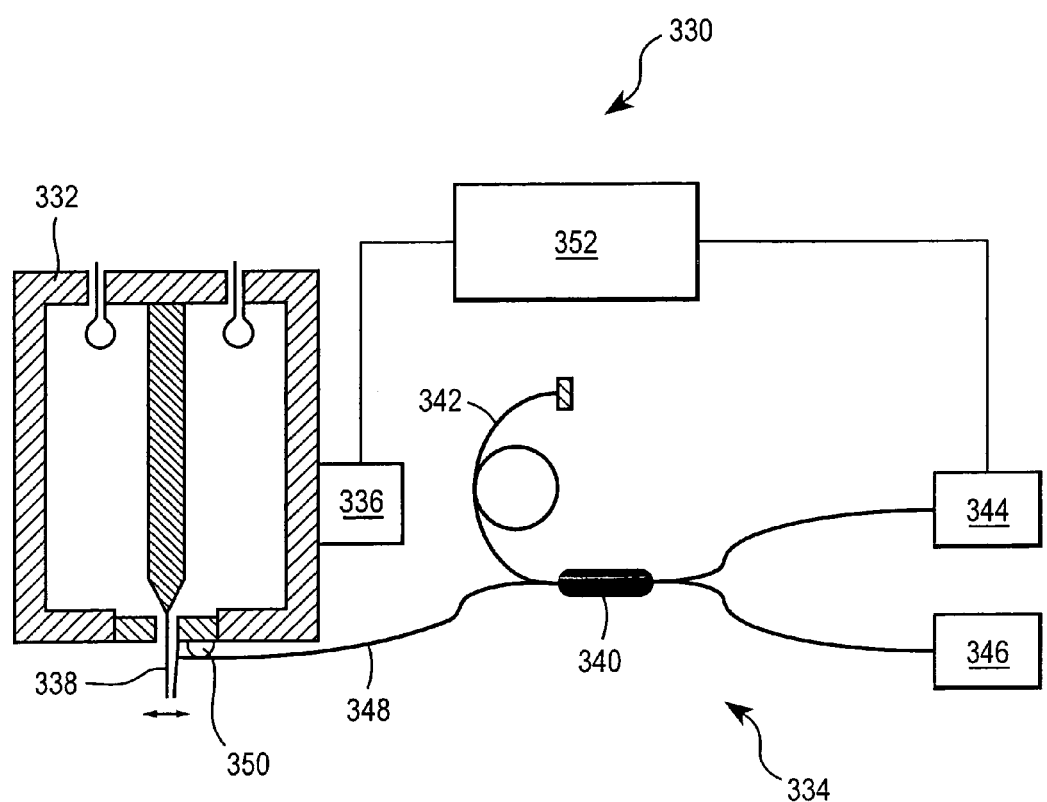
FIG. 20 schematically illustrates another exemplary embodiment of an evanescent wave probe integrated with a scanning probe microscope.

Interferometer detection: A fiber optic interferometer with 1×2 or 2×2 coupler is used to detect the probe bending or vibration amplitude. One flat fiber end of the fiber interferometer is positioned near the front end of the probe. The interference between the reflected light from the probe and the internal reflection of the interferometer can be detected to monitor the probe displacement. For an interferometer with 1×2 coupler, the internal reflection is from the flat fiber end which is facing the probe. For an interferometer with 2×2 coupler, the internal reflection can be the reflection from the other fiber end. Other types of interferometer setups can also been used. An example is illustrated in FIG. 20, discussed further below.

Diffraction beam detection: This method is generally used for shear force mode. The laser beam is focused on the probe and the diffraction spot is detected by a PSPD on the opposite side the probe. When the vibration property of the probe changes due to the shear force, a corresponding change on the diffraction light can be detected by the PSPD.

Exemplary Non-Optical Detection Methods.

Electron tunneling current detection: An electrode is positioned on the metalized back side of AFM probe, the tunneling current between electrode and the AFM probe can be detected so as to know the bending or vibration information of the AFM probe.

Tuning fork detection: The tuning fork is a piezoelectric device which can convert mechanical bending to the electric signal directly. The tuning fork is also a high Q resonant device which is very sensitive to the external force added on either one of its two arms. To detect the atomic force or shear force, one arm of the tuning fork is attached to the probe. The force sensed by the probe can transfer to the tuning fork arms and can be detected by the electronics used to drive the tuning fork.

Other piezoelectric device: Other types of piezoelectric devices can be used to replace the tuning fork as the force sensor. These devices are specially designed to adapt to various types probes and probe constructions.

Piezo-resistive device (e.g., strain gauge detector): The resistance of such device is corresponding to the mechanical strain, which can be used to detect the atomic force instead of the piezoelectric device. An extra piezoelectric device is still need to be used here to generate the mechanical vibrating in AC mode.

Microwave detection: EMP is not only sensitive to the sample impedance, but is also very sensitive to the probe sample distance. The small metal tip protruding from a microwave resonator can be positioned near the SPM probe so that a small capacitance can be built up between them. The bending or vibration of the SPM probe changes the gap between the two probe so that the capacitance between them changes correspondingly. Similar to the principle of EMP, this capacitance change introduces a change in the resonant frequency of the resonator which can be detected by the microwave detection circuits.

All of the exemplary methods and systems disclosed and described herein can be used with EWP systems and devices to form an EWP-SPM combined system. In addition, an EWP-Impedance-SPM combined systems and methods can be formed.

FIG. 19 schematically illustrates an exemplary embodiment of an evanescent wave probe integrated with a scanning probe microscope to result in both spin resonance and scanning probe capability. The exemplary embodiment 300 includes an evanescent wave probe 302 and a scanning probe microscope 304. The evanescent wave probe 302 can be any suitable evanescent wave probe, such as those disclosed and described herein with respect to FIGS. 7A-7B and 11-14B. The scanning probe microscope 304 can be any suitable scanning probe microscope, such as those listed and discussed with respect to Table 1.

In the exemplary embodiment 300, the scanning probe microscope is illustrated as an atomic force microscope with optical detection using a reflected beam. A piezo stack 306 is mounted or coupled to the evanescent wave probe 302. The piezo stack 306 drives the tip 308 of the evanescent wave probe 302 near the tip's mechanical resonant frequency. For shear force mode, the vibration is parallel to the sample surface and perpendicular to the propagation direction of a laser beam emitted from a focused laser source 310. The laser beam and the tip 308 interact in the region of the sample. An atomic force, such as a shear or normal force, is detected by monitoring a change in deflection or position of the tip 308 detected by a sensor 312, such as a quadrant photo diode, as the deflection of the laser from the tip changes. A controller 314, such as a low frequency resonant detection circuit, integrates the control and detection functions of the system.

FIG. 20 schematically illustrates another exemplary embodiment of an evanescent wave probe integrated with a scanning probe microscope to result in both spin resonance and scanning probe capability. The exemplary embodiment 330 includes an evanescent wave probe 332 and a scanning probe microscope 334. The evanescent wave probe 332 can be any suitable evanescent wave probe, such as those disclosed and described herein with respect to FIGS. 7A-7B and 11-14B. The scanning probe microscope 304 can be any suitable scanning probe microscope, such as those listed and discussed with respect to Table 1.

In the exemplary embodiment 330, the scanning probe microscope is illustrated as an atomic force microscope with optical detection using interference detection. A piezo stack 336 is mounted or coupled to the evanescent wave probe 302. The piezo stack 336 drives the tip 338 of the evanescent wave probe 332 near the tip's mechanical resonant frequency. For shear force mode, the vibration is parallel to the sample surface. An atomic force, such as a shear or normal force, is detected with an interferometer 340, such as a fiber interferometer, by monitoring a change in interference pattern between reflected light from the tip 338 and light reflected from the reference arm 342 and detected by a sensor 344, such as a photo diode. The reflected light is supplied by a source 346, such as a laser, and directed to the tip 338 by the sample arm 348. The sample arm can optionally be mounted to the evanescent wave probe by any suitable means, such as by adhesive 350. A controller 352, such as a low frequency resonant detection circuit, integrates the control and detection functions of the system.

By adding the relative detecting features, EMP can also be integrated with other SPMs. An exemplary embodiment is the combination with scanning tunneling microscope (STM). By isolating the microwave resonator probe from the microwave input/output coupler, the bias voltage and current amplifier can be connected to the tip to enable the STM mode. Another exemplary embodiment is the combination with scanning near-field optical microscope. This combination can be realized by changing the metal tip of the EMP into a tapered fiber with a metal coating with a <100 nm fiber aperture at the end. A further exemplary embodiment is the combination with the magnetic force microscope (MFM). This can be realize by attaching a metal coated magnetic particle at the tip end of the EMP.

Further in addition to the above disclosed and described methods and systems including combinations thereof, the methods and systems described in U.S. Provisional Application No. 60/546,056, entitled "Integration of AFM/STM into Evanescent Microwave Probe" filed on Feb. 18, 2004, the entire contents of which are incorporated herein by reference, can be used in the methods, systems and combinations described herein. These methods and systems are further described below.

Atomic force sensor or scanning tunneling microscope probe can be integrated into an evanescent microwave probe (EMP) to form a microscope with the capability of regulating tip-sample distance through atomic force or tunneling current and obtaining simultaneous topology and electrical impedance images.

The describe methods and designs to integrate AFM/STM sensors into evanescent microwave probe. A metal or metalized conductive tip will act both as EMP tip and AFM/STM tip.

In AFM integrated EMP system (EMP-AFM), the EMP tip is either the center conductor of EMP resonator itself or a small metal coated insulating element attached to the center conductor of EMP resonator, with which the microwave signal and atomic force will all be sensed. The atomic force signal can be read out in two ways: electric detection or optical detection. And there are also two operation modes, DC mode, in which the deflection of EMP tip due to the tip-sample atomic force is detected directly, and AC mode, in which the EMP tip is oscillated in or near its resonant frequency and the change of oscillation amplitude, resonant frequency or quality factor will be detected.

In the situation of STM integrated EMP system (EMP-STM), the center conductor tip of EMP is used directly as STM tip. However, to de-couple the interference between microwave signal and tunneling current signal, the EMP resonator coupling loops are designed to be insulated from the resonator cavity.

In one embodiment, a force sensor with electrical read out is attached to the tip of EMP probe and atomic force is sensed by change in sensor mechanical resonant frequency, vibrating amplitude or quality factor. Such sensor can be piezoelectric or piezo-resistive (strain gage sensor). The sensor can be bulk material devices, such as a quartz tuning fork, or thin/thick film device, such as a cantilever coated with piezoelectric or piezo-resistive materials. In this case, the integration of force sensors is possible since the sensors are very small and read out is through electrical signals from piezoelectric or piezo-resistive effect. In the second embodiment, a small force cantilever is mounted near the EMP tip and cantilever tip is electrically connected to the EMP tip. The force is sensed by cantilever through deflection or changes in mechanical resonant frequency, amplitude or Q of the cantilever detected by laser beam deflection. A special configuration is designed in this case to mitigate the conflict between microwave signals of EMP and optical read out signal for cantilever.

In exemplary embodiments, an EMP tip and an AFM/STM tip are combined together so that the microwave signal and AFM/STM signal will be detected simultaneously.

Two example methods to integrate AFM with EMP are disclosed herein, but any suitable integration method can be used. In a first design, the center conductor of EMP resonator is extruded out of EMP cavity and acts as both EMP and atomic force sensing tip. Two techniques can be used to detect the deflection or oscillation of EMP tip. One is to attach a small piezo-electric or piezo-resistive unit to the EMP tip and measure the electric signal resulted from the tip deflection or oscillation. Another technique is to focus a laser beam on a portion of EMP tip and detect the movement of reflected laser beam. For the optical detection scheme, the shape of EMP resonator need to be specially designed to allow the laser beam to pass.

In a second design, an insulating cantilever with tip coated with conductive film is attached to the center conductor of EMP resonator. The metalized tip is electrically connected to the center conductor, which allows the microwave signal to be carried on. The AFM signal can also be read out electrically or by optical means as in the first design.

There are two operation modes for AFM signal detection. In DC mode, the EMP tip contacts with sample during operation. The defection of EMP tip or cantilever due to atomic force is detected. In AC mode, The EMP tip or cantilever is driven by a piezoelectric unit to vibrate in the frequency same as or close to its resonant frequency. The driving piezoelectric unit can be attached to the EMP tip of cantilever directly or to the whole EMP resonator. The change of amplitude, resonant frequency or quality factor of the vibrating tip/cantilever due to atomic force change is detected electrically or optically. In this operation mode, the EMP tip is usually in non-contact with the sample.

Figure 21A:
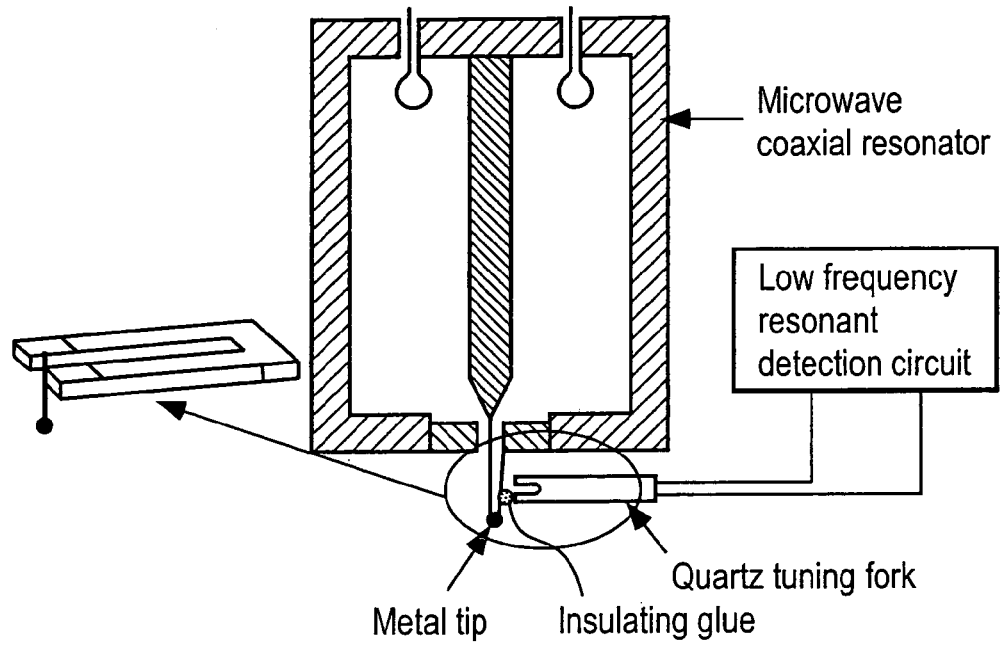
FIGS. 21A and 21B shows an example of EMP-AFM integration, where the quartz tuning fork is mounted with one arm stick with the tip of the microwave resonator as force detector. (a) is working on shear force mode with tuning fork mounted horizontally; (b) is working on normal atomic force mode with tuning fork mounted vertically.
Figure 21B:
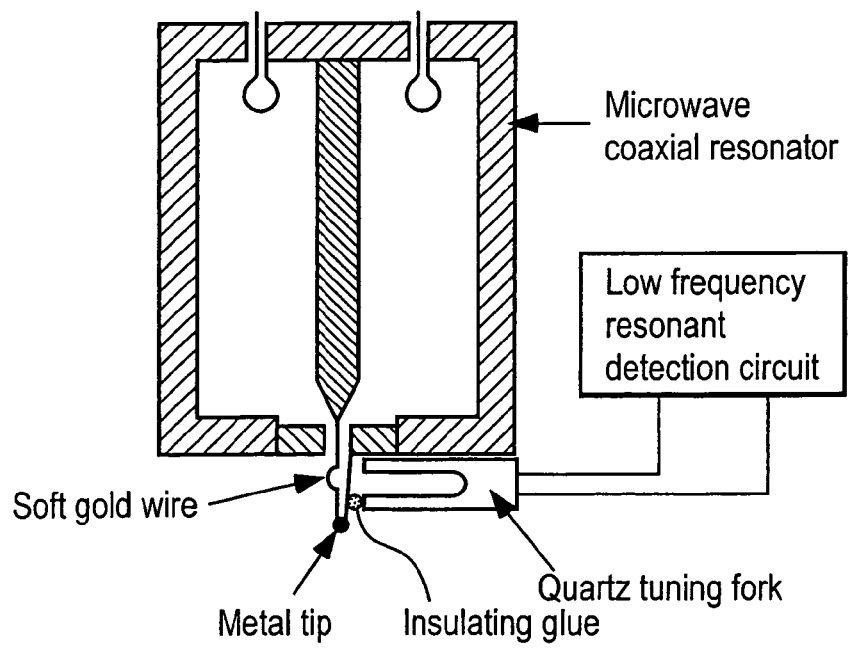

FIGS. 21A and 21B illustrate examples of AFM-EMP integration using a quartz tuning fork as a driving and detection unit at the same time. Preferred configuration of evanescent microwave probe is a dielectrics (or air) filled coaxial resonator with high Q factor in order to achieve high sensitivity. The tip of the EMP is a thin metal wire connected to the center conductor and extruding from a small aperture of end shielding wall (with a preferred outside length of <2 mm). The shielding wall is formed by a metallic thin film (~1-5 microns) deposited on a low loss and low dielectric constant material, such as sapphire. The metal thin film is electrically connected to the outer conductor of the resonator. The tuning fork is fabricated from quartz, such as the one used in commercial clocks/watches or customized. The size of the tuning fork should be as small as possible in order to have high force sensitivity. The adhesive used to attach the EMP tip to one arm of the tuning fork should have low microwave and mechanical loss and be used as little as possible to reduced the effect on tuning fork frequency and Q. The vibration direction of the tuning fork can be either horizontal (shear force as respect to the sample surface, which is shown as FIG. 21A) or vertical (normal atomic force, which is shown as FIG. 21B). The wire from the center conductor of EMP to tuning fork should be thin and soft so that it will not limit the vibration of the tuning fork. The section from the tuning fork to the tip should be short so that the force sensed by the tip can be coupled effectively to the tuning fork. The base of the tuning fork is fixed to the EMP resonator rigidly.

Figure 22:
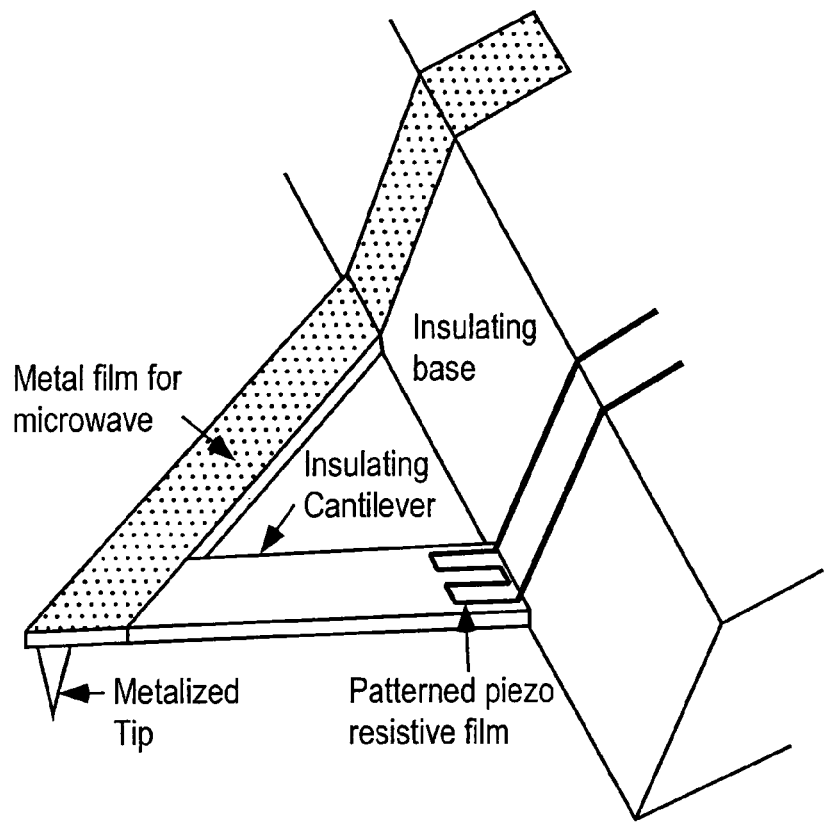
FIG. 22 shows the detail structure of an exemplary cantilever that can be used to transmit microwave signal and detect atomic force simultaneously. A piezo-resistive film is coated to detect the deflection (strain) of the cantilever.

FIG. 22 is another example of AFM signal detection with cantilever and piezo-resistive read-out mechanism. A cantilever is attached to the EMP resonator. The microwave signal from EMP is transmitted to the metalized tip through a metal film coated on one arm of the cantilever. A patterned thin film is coated on another arm of the cantilever with piezoelectric materials to form a strain gage device. When the cantilever is bended by atomic force between tip and the sample, the resistance of the strain gage will change and can be detected by the electronics. The cantilever materials are preferably made of insulating materials such as quartz, glass or silicon nitride since insulating materials will not affect microwave signal of EMP. Other kind of strain gage sensors can also be used here, such as metallic strain gage or silicon strain gage sensors. In order to prevent influence of to the EMP signals, an insulting buffer piece will be used between EMP tip and sensor.

Figure 23:
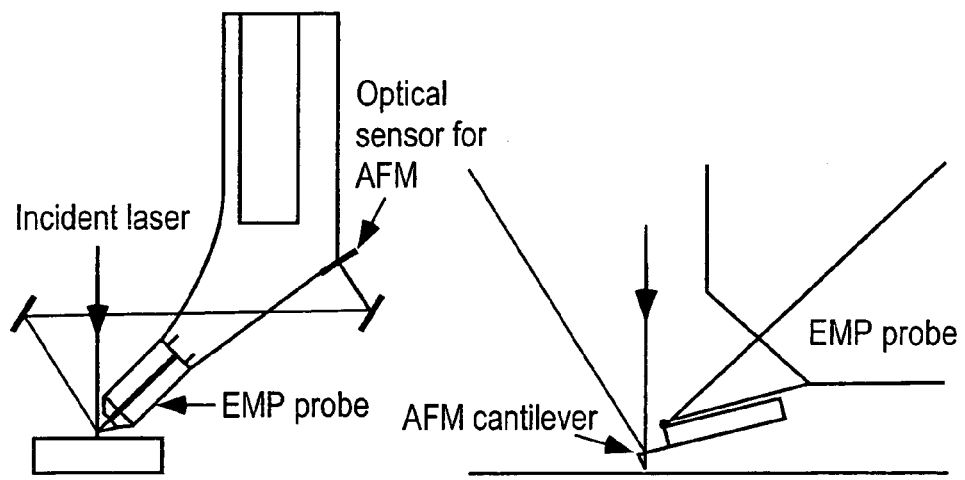
FIG. 23 shows an example of EMP-AFM integration, where an AFM cantilever is attached to the EMP probe as atomic force sensor. The deflection of the cantilever is detected by optical laser beam.

In FIG. 23, an optical detection scheme is used. The EMP is mounted to a fixture, which can then be attached to a scanner. An AFM cantilever is then attached to the EMP probe as shown in the detailed drawing in the right part of FIG. 23. The EMP tip is electrically connected to the tip of AFM cantilever by a thin conducting path. The total connection length from the aperture to the cantilever tip should be as short as possible to achieve high microwave sensitivity, and long enough to allow the laser beam to have access to the tip of the cantilever and reflected to the optic sensor. The total setup can detect the small deflection of AFM cantilever tip in the same way as in ordinary AFM instrument, which has the advantage of easy to integrate EMP to commercial AFM systems.

Figure 24:
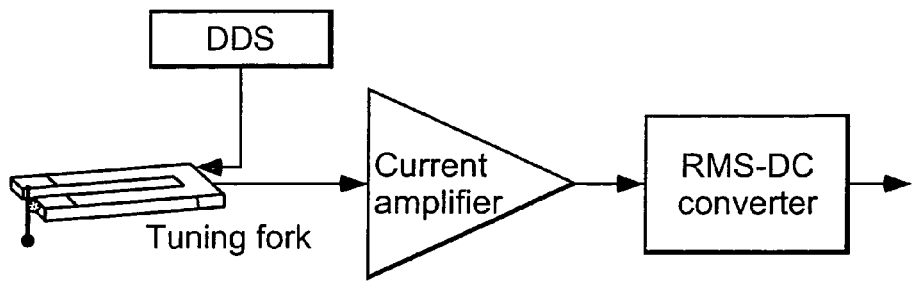
FIG. 24 shows a schematic view of exemplary electronics based on RMS-DC converter, which can be used to translate oscillation signal generated by the tuning fork to DC voltage signal.

For AC mode operation, an electronic circuit is required to drive the force sensor and convert its signal to voltage signal, which can be acquired by the control electronics of the system. The required electronic circuit is determined by the type of force sensor. For example, when a tuning fork is used as the force sensor, the atomic force may change the resonant frequency, Q or amplitude of the tuning fork. Several circuit designs can measure such changes, such as RMS-DC converter, Lock-in electronics, or Phase Lock Loop (PLL) device. FIG. 24 shows a design based on the RMS-DC converter. The DDS generate sinusoidal wave to drive the tuning fork at a fixed frequency. The current amplifier will read output. When the tuning fork is driven at resonant frequency, the output signal from the current amplifier has the maximum amplitude. The RMS-DC converter the AC signal to DC voltage with the value equals to the Root Mean Squire (RMS) of the AC signal. When the tip sample is close enough, the atomic force will drag the resonant frequency down, and the driven frequency is no longer equals to the resonant frequency. As a result, the output of the RMS-DC converter will drop down, which can be used as an effective signal to monitor the atomic force.

Figure 25:
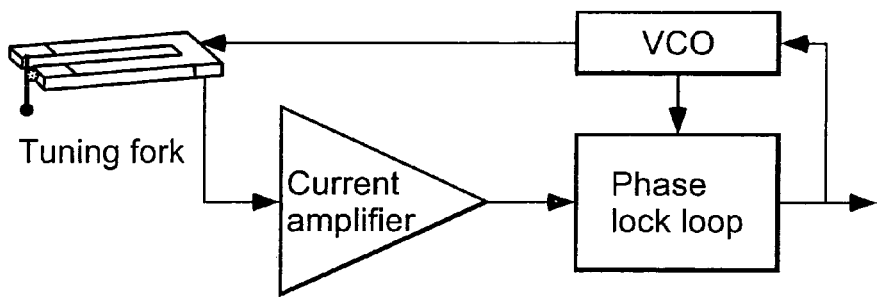
FIG. 25 shows another schematic view of the exemplary electronics based on Phase Lock Loop, which can also be used to track the resonant frequency of tuning fork.

FIG. 25 shows another electronic design to detect the atomic force signal. A Phase Lock Loop (PLL) and a Voltage Controlled Oscillator (VCO) are used to follow the resonant frequency of the resonator. By monitoring the DC control voltage of VCO, the change in resonant frequency caused by the atomic force can be detected.

Figure 26:
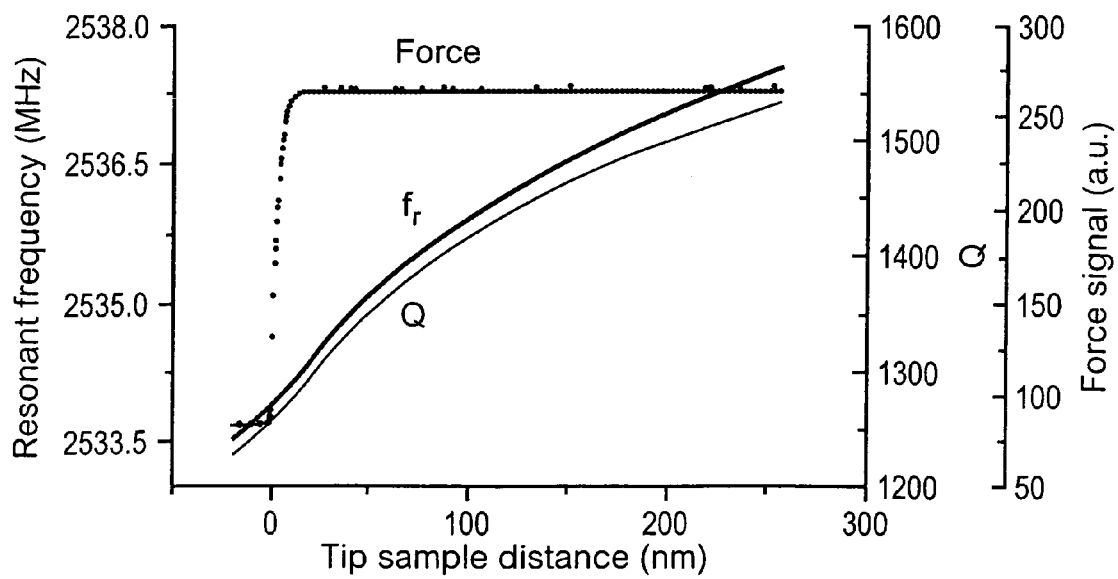
FIG. 26 shows an exemplary approaching curve obtained by the exemplary EMP-AFM system. The resonant frequency, Q of EMP and the force signal are measured simultaneously as function of tip-sample distance.

A real EMP-AFM system based on the tuning fork design has been built and tested. FIG. 26 shows the approaching curve of EMP resonant frequency, Q and atomic force signal as the tip-samples distance is in the range of 300 nm. The tuning fork is used as force sensor to detect shear force as shown in FIG. 21A. The electronic circuit is designed as shown in FIG. 24. As shown, the typical atomic force signal appears when tip sample distance is smaller than about 10 nm, while the microwave signal $f_r$ and Q drops continuously when the tip approaching to the sample. When atomic force signal drop to the bottom, a slightly trend change in $f_r$ and Q signal appears too, which means the tip is in contact with the sample. The sharp drop of the atomic force signal can be used as feedback signal to control the tip-sample distant at a constant value (smaller than 10 nm).

Figure 27:
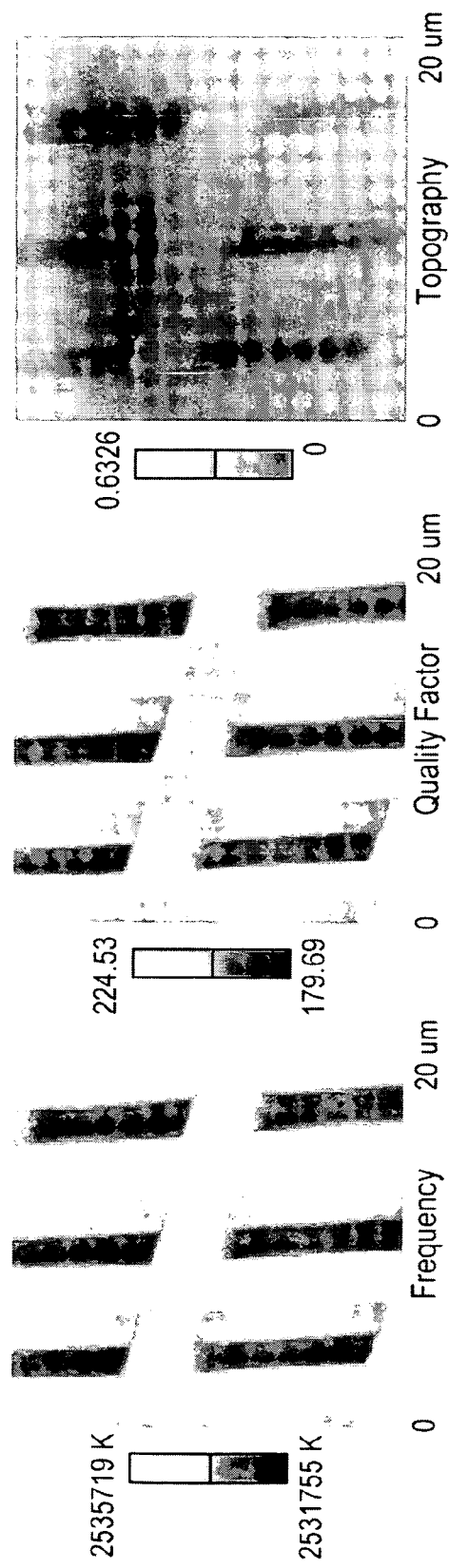
FIG. 27 shows the simultaneous images of microwave and topography obtained by the exemplary EMP-AFM system.

FIG. 27 shows the images of $f_r$, Q and topography scanned by EMP-AFM working in constant force mode. A standard AFM sample is used for the scanning. The sample is patterned with squire holes by low conductive film. The period in X and Y direction are all 10 μm. The step structures shown in each square in the topography image implies the thickness of the film is changing. Since the sheet resistance is determined by the conductivity and the thickness of the film. The $f_r$ and Q images also shown similar structure. An obvious tilting of the sample alignment can be observed in the topography image, but doesn't shown in $f_r$ and Q images, which means the feed back is working very well.

Figure 28:
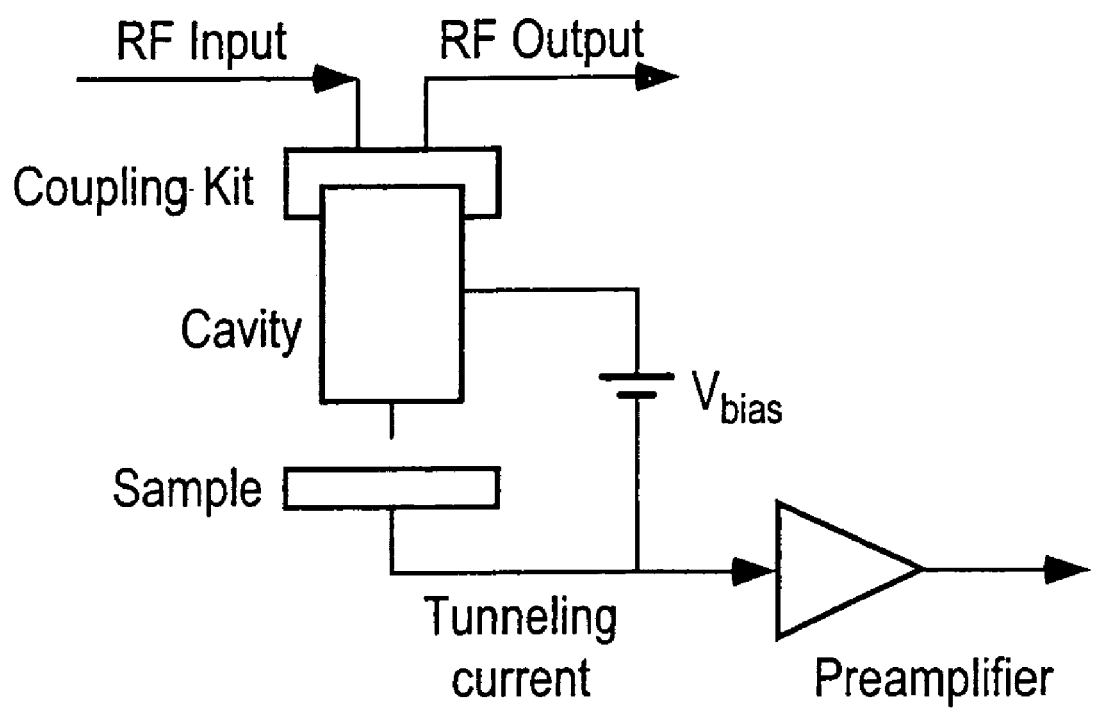
FIG. 28 shows a scheme of an exemplary STM-EMP probe structure.

STM with EMP can be integrated. As shown in the exemplary embodiment of FIG. 28, an EMP tip is electrically connected to tunneling current detection circuit and will simultaneously perform STM measurement. The microwave resonator probe is electrically isolated from microwave input/output coupler so that bias voltage and current amplifier can be connected to the tip to enable STM mode. Microwave signal is coupled into or out from the resonator through an isolated coupling kit. During measurement, the tunneling current can be used as a feedback signal to regulate the tip-sample distance.

Applications: Spatially resolved spin detection can be used to study a broad range of materials and biological specimens in much finer detail than has been available.

The technique can be used for high throughput screening of combinatorially synthesized compounds to identify specific chemical bonding and other spin resonance related signatures in the compounds.

Where ferromagnetic spin resonance is of interest, the invention provides a direct readout of real and imaginary parts of the RF permeability for extremely small specimen volumes of ferro- or ferrimagnetic materials. A line width associated with ferromagnetic resonance response (FMR) of a single crystal of yttrium-iron garnet (YIG), illustrated graphically in FIG. 15A, approaches the practical limit of less than 1 Oe at room temperature for commercially available chemical purity and crystal perfection. YIG and similar ferrimagnetic and ferromagnetic compounds can be used to "tag" a suitable target compound in order to more easily sense the presence or condition of the target compound.

Accurate measurement of the resonance frequency can be used to monitor small changes in specimen magnetization (magnetic moment/volume), magnetic anisotropy, mechanical strain (magneto-restriction) and/or shape anisotropy. Magnetization and magnetic anisotropy are also very sensitive to temperature, and FMR probes have been investigated for use as thermometers. The peak of the resonance line is also proportional to the ratio of magnetization to intrinsic line width (for a Lorentzian shape spectrum). As such it sensitively characterizes variations in chemical composition, structural homogeneity, and polaronic charge from the magnitude of the circuit Q and the degree of Gossip line broadening.

Another important application is the detection of small (nm to µm size) ferromagnetic, super-paramagnetic, or light-pumped spin-populated semiconductor particles. These particles can be used, for example as fluorescent particles, in bioscience, as tagging particles (when the appropriate chemical bonding is used to link the particle with molecules, pathogens, DNA's, proteins and other biological reagents) and/or as contrst agents to diagnose or to identify structure, activity and other biological properties. Examples of magnetic particles suitable for this use include those disclosed in U.S. Provisional Patent Application No. 60/447,097, filed on Feb. 13, 2003, the entire contents of which are herein incorporated by reference.

For this application, high sensitivity of the detection technique is extremely important. Because room temperature detection is crucial, high spin population of the particles and long spin relaxation time at room temperature are also important. Choice of materials for the tagging particles is, therefore, also important. The criteria for particle materials are narrow spin resonance (i.e., long relaxation), high g factor, non-metallic and high ferromagnetic magnetization at room temperature. The high Q made possible by the narrow-line width specimens such as highest purity Yttrium Ion Garnet (YIG), YIG substituted with aluminum, gallium or indium, or certain spinel compounds such as lithium ferrite, are examples of suitable choices for the particle materials. Furthermore, changes in (narrow) line widths can also be used to sense changes induced by adsorbed magnetic molecules on the surface or chemical bonding. For this application, the largest practical surface-to-volume ratio is desirable. Ferrite materials, such as YIG, also have the advantages of non-air sensitive as in metallic particles, and robust ferromagnetic properties as particles size decreases. A ferrite molecule is attached to at least one molecule whose presence or absence in a collection of molecules is of interest, and a selected portion of the collection is interrogated using spatially resolved spin resonance detection: If spin resonance (1) is detected or (2) is not detected, this condition is interpreted as indicating that (1) the molecule of interest is present or (2) the molecule of interest is present, if at all, in a concentration that is below a detection threshold for the spin resonance detection, respectively.

Advantages of using detection of spin resonance of small particles, such as YIG or lithium ferrite, include the following: (1) Discrimination between specific bonding and non-specific bonding. Magnetic force of ferromagnetic particles and influence of spin resonance frequency (field) can all be used to discriminate between of specific and non-specific bonding; (2) Because different materials have different spin resonance (frequency-magnetic field relationship), this technique will provide "multi-color" capability as in a luminescent tagging technique. This response is in contrast to the magnetization detection technique for simple magnetic particle tagging, where only one property, magnetization, is measured and cannot be used to distinguish different types of tagging particles or agents.

The exemplary embodiments of spatially resolved NMR described herein are a powerful tool for determining the structure of organic chemicals, especially the structure of protein, proteomics targets or polypeptides. An example application is the high throughput screening of the structure of proteins. Examples of preferred biological or chemical samples are selected from a group consisting of proteomics, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides; organic and inorganic compounds in fluid or condensed matter forms.

The spatially resolved NMR described in the exemplary embodiments herein has the advantage of providing imaging and spectroscopy simultaneously. Different information in the NMR spectrum can be used to calculate the structure of proteins: the chemical shifts, the peak splitting patterns and the intensities of the resonant peaks. Conventional simulation techniques can be used for the calculation of the structure through the spectrum. In order to get 1D, 2D and 3D structure of the target proteins, the protein is labeled in different ways in order to get more spectrum information. Conventional NMR labeling material can be used, such as $^{15}N^-$, $^{13}C^-$, $^2H^-$, $^1H^-$ or any of their combination.

Protein structure determination is important in several ways. The structures confirm the evolutionary changes in the primary structure of a given protein from related species, which lead to genetic disorder and diseases at the molecular level. Clear understanding of the nature of these diseases depends upon precise structure determination of the concerned proteins. Also, when the structure of an enzyme is determined, a suitable inhibitor of the active site can be designed through combinatorial chemistry, computer modeling and docking techniques. This structure based drug design promises efficient drugs for several diseases, in a short time. The function of a protein is directly linked to its 3-D structure, which has been proved by several lines of examples and evidences. Highly resolved structures can lead to very clear understanding of the functions of these molecules. The structure function relationship is the key to our knowledge of biology and the biological world.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. An apparatus for spatially resolved impedance in a material sample, the apparatus comprising: an evanescent wave probe positionable adjacent to a sample location, the evanescent wave probe configured to generate an evanescent wave including at least one of a time varying amplitude and a time varying phase, a detection circuit, the detection circuit detecting a time-resolved change in a resonance frequency of the evanescent wave probe and of a change in a quality factor of the evanescent wave probe; and a processing system, the processing system processing the change in the resonance frequency and the change in a quality factor to produce an impedance measurement.

2. The apparatus of claim 1, comprising an atomic force measuring device, the atomic force measuring device measuring an atomic force between a tip of the evanescent wave probe and a surface of a sample in the sample region to determine at least one of a topography of the surface of the sample in the sample region and a distance between the tip of the evanescent wave probe and the surface of the sample.

3. The system of claim 2, wherein the measured atomic force includes a shear force.

4. The system of claim 2, wherein the measured atomic force includes a normal force.

5. A method of measuring a spatially resolved impedance in a material sample, the method comprising: moving a tip of an evanescent wave probe toward a surface of a sample to place the surface of the sample within a sensing distance; generating an evanescent wave with the evanescent wave probe, the evanescent wave including at least one of a time varying amplitude and a time varying phase; making a time resolved measurement of a change in a resonant frequency of the evanescent wave probe and of a change in a quality factor of the evanescent wave probe; and determining an impedance of the sample based on the change in the resonant frequency and based on the change in the quality factor.

6. The method of claim 5, comprising measuring an atomic force between a tip of the evanescent wave probe and a surface at the first location to determine at least one of a topography of the surface of the sample at the first location and a distance between the tip of the evanescent wave probe and the surface of the sample.

7. The method of claim 6, wherein measuring the atomic force includes measuring a shear force.

8. The method of claim 6, wherein measuring the atomic force includes measuring a normal force.

9. A method of screening a plurality of biological, chemical or material samples, the method comprising: making a plurality of spatially resolved impedance measurements corresponding to the plurality of samples according to claim 5; and selecting at least one of the plurality of samples based on the plurality of spatially resolved impedance measurements.

* * * * *